US008197807B2

(12) United States Patent
Brenner

(10) Patent No.: US 8,197,807 B2
(45) Date of Patent: Jun. 12, 2012

(54) NICOTINAMIDE RIBOSIDE KINASE COMPOSITIONS AND METHODS FOR USING THE SAME

(75) Inventor: Charles M. Brenner, Lyme, NH (US)

(73) Assignee: Trustees of Dartmouth College, Hanover, NH (US)

( * ) Notice: Subject to any disclaimer, the term of this patent is extended or adjusted under 35 U.S.C. 154(b) by 213 days.

(21) Appl. No.: 11/912,400

(22) PCT Filed: Apr. 20, 2006

(86) PCT No.: PCT/US2006/015495
§ 371 (c)(1),
(2), (4) Date: Nov. 20, 2007

(87) PCT Pub. No.: WO2006/116322
PCT Pub. Date: Nov. 2, 2006

(65) Prior Publication Data
US 2008/0206221 A1    Aug. 28, 2008

(51) Int. Cl.
*A61K 38/45* (2006.01)
*C07H 17/00* (2006.01)
*A61P 35/00* (2006.01)
(52) U.S. Cl. .............. 424/94.5; 514/45; 514/25; 435/15
(58) Field of Classification Search .................. None
See application file for complete search history.

(56) References Cited

U.S. PATENT DOCUMENTS 7,491,743 B2 *  2/2009  Cuny et al. ............... 514/397

FOREIGN PATENT DOCUMENTS

WO            0132888       5/2001

OTHER PUBLICATIONS

Saunders et al 1 Tiazofurin is phosphorylated by three enzymes from Chinese Hamster Ovary Cells. Cancer Research 50, 5269-5274, Sep. 1, 1990.*
Saunders et al 2 Phosphorylation of 3-Deazaguanosine by nicotinamide riboside kinase in Chinese Hamster Ovary Cells.*
Tanimori et al, Bioorganic. Med. Chem Lett. 12:1135-1137, 2002.*
Stubberfield et al NAD+ depletion and cytotoxicity in isolated hepatocytes. Biochemical Pharmacology 1988; 37(20): 3967-74 Abstract included.*
Stubberfield et al (NAD+ depletion and cytotoxicity in isolated hepatocytes (Biochemical Pharmacology 1988; 37(20): 3967-74 see abstract.*
Berger NA et al. (Poly (ADP-ribose in the cellular response to DNA damage), Radiation research Jan. 1985; 101(1): 4-15 see abstract.*
Berger et al., "Modulation of Nicotinamide Adenine Dinucleotide and Poly(Adenosine Diphosphoribose) Metabolism by the Synthetic "C" Nucieoside Analogs, Tiazofurin and Selenazofurin", J. Clin. Invest. 1985 75:702-705.
Han et al., "Cellular Uptake Mechanism of Amino Acid Ester Prodrugs in Caco-2/hPEPT1 Cells Overexpressing a Human Peptide Transporter", Pharmaceutical Research 1998 15(9):1382-1386.
Genbank Accession No. AK001663 Jan. 9, 2008.
Genbank Accession No. YNL129W—Nov. 7, 2005.
NCBI Accession No. NP_060351 [gi:8923530] with Revision History Jul. 4, 2000-Jun. 3, 2007.
NCBI Accession No. NP_733778 [gi:24762248] with Revision History—Nov. 2, 2002-Jul. 5, 2007.
NCBI Accession No. NM_017881 [gi:8923529] with Revision History—Jul. 4, 2000-Nov. 17, 2006.
NCBI Accession No. AK000566 [gi:7020748] with Revision History—Feb. 22, 2000-Sep. 12, 2006.
NCBI Accession No. BC001366 [gi: 33876100] with Revision History—Dec. 12, 2000-Jul. 15, 2006.
NCBI Accession No. BC036804 [gi:22477870] with Revision History—Aug. 26, 2002-Mar. 25, 2004.
NCBI Accession No. BC026243 [gi:20072207] with Revision History—Apr. 8, 2002-Mar. 25, 2004.
NCBI Accession No. NM_170678 [gi:24762247] with Revision History Nov. 7, 2002-Nov. 17, 2006 NM_170678.2 which replaces NM_170678 is provided.
NCBI Accession No. CAG61927 [gi:49528270] with Revision History—Jun. 30, 2004-Nov. 14, 2006.
NCBI Accession No. Z71405 [gi:1302065] with Revision History—May 6, 1996v-Aug. 11, 1997.
NCBI Accession No. AX877238 [gi:40031974]—Dec. 17, 2003.
NCBI Genbank Accession No. AX877238 [gi:40031974]Dec. 17, 2003.
Bieganowski et al., "Discoveries of Nicotinamide Riboside as a Nutrient and Conserved NRK Genes Establish a Preiss-Handler Independent Route to NAD+ in Fungi and Hunams", Cell 2004 117:495-502.
Farquhar et al., "Synthesis and antitumor evaluatiobn of bis[(pivaloyloxy)methyl]2'-deoxy-t-fluoroudine 5'-monophosphate (FdUMP):a stategy to introduce nucleotides into cells", J Med Chem 1994 37(23):3902-3909.
Sasiak et al., "Purification and Properties of a Human Nicotinamide Ribonucleoside Kinas", Archives of Biochemistry and Biophysics 1996 333(2):414-418.
Saunders et al., "Phosphorylation of 3-Deazaguanosine by Nicotinamide Riboside Kinse in Chinese Hamster Ovary Cells", Cancer Research 1989 49:6593-6599.
Bieganowski et al., "Eukaryotic NAD+ Synthetase Qns1 Contains an Essential, Obligate Intramolecular Thiol Glutamine Amidotransferase Domain Related to Nitrilase", J. Biol. Chem. 2003 278(35):33049-33055.
Boon et al., "An anatomy of normal and malignant gene expression", Proc. Natl. Acad. Sci. 2002 99(17):11287-11292.
Burkle, Alexander, "Physiology and pathophysiology of poly(ADP-ribosyl)ation", BioEssays 2001 23:795-806.
Fleischmann et al., "Whole-Genome Random Sequencing and Assembly of *Haemophilus influenzae* Rd", Science 1995 269:496-512.
Gingrich et al., "Codehydrogenase I and other Pyridinium Compounds as V-Factor for *Hemophilus influenzae* and *H. parainfluenzae*", J. Bacteriol. 1944 47:535-550.
Godek et al., "In Vitro Evaluation of Nicotinamide Riboside Analogs against *Haemophilus influenzae*", Antimicrobal Agents and Chemotherapy 1990 34(8):1473-1479.

(Continued)

*Primary Examiner* — Kagnew H Gebreyesus
(74) *Attorney, Agent, or Firm* — Licata & Tyrrell P.C.

(57) ABSTRACT

The present invention relates to isolated nicotinamide riboside kinase (Nrk) nucleic acid sequences, vectors and cultured cells containing the same, and Nrk polypeptides encoded thereby. Methods for identifying individuals or tumors susceptible to nicotinamide riboside-related prodrug treatment and methods for treating cancer by administering an Nrk nucleic acid sequence or polypeptide in combination with a nicotinamide riboside-related prodrug are also provided. The present invention further provides screening methods for isolating a nicotinamide riboside-related prodrug and identifying a natural source of nicotinamide riboside.

3 Claims, 1 Drawing Sheet

OTHER PUBLICATIONS

Holdsworth et al., "A fraction derived from brewer's yeast inhibits cholesterol synthesis by rat liver preparations in vitro", British Journal of Nutrition 1991 65:285-299.

Leder et al., "Synthesis of Nicotinamide Mononucleotide by Human Erythrocytes in Vitro", J. Biol. Chem. 1951 189:889-899.

Li et al., "A Novel Muscle-specific Beta1 Integrin Binding Protein (MIBP) that Modulates Myogenic Differentiation", J. Cell Biol. 1999 147:1391-1397.

Li et al., "The muscle integrin binding protein (MIBP) interacts with alpha7Beta1 integrin and regulates cell adhesion and laminin matrix deposition", Developmental Biology 2003 261:209-219.

Saunders et al., Tiazofurin Is Phosphorylated by Three Enzymes from Chinese Hamster Ovary Cells, Cancer Research 1990 50:5269-5274.

Shifrine et al., "A Growth Factor for *Haemophilus* Species secreted by a Pseudomonad", Nature 1960 187:623.

Ziegler, Mathais, "New functions of a long-known molecule—Emerging roles of NAD in cellular signaling", Eur. J. Biochem. 2000 267:1550-1564.

Sasiak et al., "Purification and Properties of a Human Nicotinamide Ribonucleoside Kinase", Archives of Biochemistry and Biophysics 1996 333(2):414-418.

* cited by examiner

```
Hsapi_Nrk1    MKTFIGISGVTNSGKTTLAKNLQKHLPN---CSVISQDDFFKPES-EIETD-KNGFLQYDVL
Hsapi_Nrk2    MK-LIVGIGGMTNGGKTTLTNSLLRALPN---CCVIHQDDFFKPQD-QIAVG-EDGFKQWDVL
Scere_Nrk1    MTSKKVILVALSGCSSSGKTTIAKLTASLFTK---ATLIHEDDFYKHDN-EVPVDAKYNIQNWDSP
Spomb_Nrk1    MT-RKTIIVGVSGASCSGKSTLCQLLHAIFEG---SSLVHEDDFYKTDA-EIPV--KNGIADWDCQ
Scere_Urk1    TPYIGIGGASGSGKTSVAAKIVSSINVP-WTVLISLDNFYNPLGPEDRARAFKNEYDFDEP
Ecoli_panK    QTLMTPYLQFDRNQWAALRDSVPMTLSEDEIARLKGINEDLSLEEVAEIYLPLSRLLNFYIS Hsapi_Nrk1    EALNMEKMMSAISCWMES---ARHSVVSTDQES------------------AEEIPIL
Hsapi_Nrk2    ESLDMEAMLDTVQAWLSSPQKFARAHGVSVQPE------------------ASDTHIL
Scere_Nrk1    EALDFKLFGKELDVIKQTGKIATKLIHNNNVDDPFTKFHIDRQVWDELKAKYDSINDDKYEVV
Spomb_Nrk1    ESLNLDAFLENLHYIRDHGVLPTHLRNRENKNVAPEALIEYADIIKEFKAP-----AIPTLEQHLV
Scere_Urk1    NAINLDLAYKCILNLKEGKRTNIPVYSFVHHNRVPDK----------------NIVIYGASVV
Ecoli_panK    SNLRRQAVLEQFLGTNGQRIPYIISIAGSVAVGKSTTARVLQALLSR--------WPEHRRVELI Hsapi_Nrk1    IIEGFLLFNYKPLDTIWNRSYFLTIPYEECKRRRSTR-VYQPPD----SPGYFDGHVWPMYL
Hsapi_Nrk2    LLEGFLLYSYKPLVDLYSRRYFLTVPYEECKWRRSTR-NYTVPD---PPGLFDGHVWPMYQKYR
Scere_Nrk1    IVDGFMIFNNTGISKKFDLKILVRAPYEVLKKRRASRKGYQTLDSFWVDPPYYFDEFVYESYR
Spomb_Nrk1    FVDGFMMYVNEDLINAFDIRLMLVTDEDTLKRREARTGYITLEGFWQDPPHYFENYVWPGYV
Scere_Urk1    VIEGIYALYDRRLLDLMDLKIYDADLDVCLARRLSR-DIVSRGRDLDGCIQQWEKFVKPNAV
Ecoli_panK    TTDGFLHPNQVLKERGLMKKKGFPESYDMHRLVKFVS---DLKSGVPNVTAPVYSHLIYDVIP Hsapi_Nrk1    KYRQEMQDITWEVVY-LDGTKSEEDLFLQVYEDLIQELAKQK---------------CL
Hsapi_Nrk2    QEMEANGVEVVYLDGMKSREELFREVLEDIQNSLLNRSQESAPSPARPARTQGPGRGCGHRTA
Scere_Nrk1    ANHAQLFVNGDVEG--LLDPRKSKNIKEFINDDDTPIAKPLS------------WVCQ
Spomb_Nrk1    HGHSHLFVNGDVTGK-LLDKR-----IQLSPSSKMSVRDNVQ-----------WAIN
Scere_Urk1    KFVKPTMKNADAIIPSMSDNATAVNLIINHIKSKLELKSNEHLRELIKLGSSPSQDVLNRNII
Ecoli_panK    DGDKTVVQPDILILEGLNVLQSGMDYPHDPHHVFVSDFVDFS----------------I Hsapi_Nrk1    QVTA
Hsapi_Nrk2    RPAASQQDSM
Scere_Nrk1    EILKLCKD
Spomb_Nrk1    SILNAL
Scere_Urk1    HELPPTNQVL
Ecoli_panK    YVDAPEDLLQ
```

NICOTINAMIDE RIBOSIDE KINASE COMPOSITIONS AND METHODS FOR USING THE SAME

INTRODUCTION

This invention was made in the course of research sponsored by the National Cancer Institute (Grant No. CA77738). The U.S. government may have certain rights in this invention.

This application claims benefit of priority to PCT/US2006/015495, filed Apr. 20, 2006, which claims benefit from U.S. patent application Ser. No. 11/113,701, filed Apr. 25, 2005, now abandoned which is a continuation-in-part of PCT application No. PCT/US2005/004337, filed Feb. 9, 2005, which claims benefit under 35 U.S.C. §119 to U.S. Provisional Patent Application Ser. No. 60/543,347, filed on Feb. 10, 2004, whose contents are incorporated herein by reference in their entireties.

BACKGROUND OF THE INVENTION

Nicotinic acid and nicotinamide, collectively niacins, are the vitamin forms of nicotinamide adenine dinucleotide (NAD+). Eukaryotes can synthesize NAD+ de novo via the kynurenine pathway from tryptophan (Krehl, et al. (1945) *Science* 101:489-490; Schutz and Feigelson (1972) *J. Biol. Chem.* 247:5327-5332) and niacin supplementation prevents the pellagra that can occur in populations with a tryptophan-poor diet. It is well-established that nicotinic acid is phosphoribosylated to nicotinic acid mononucleotide (NaMN), which is then adenylylated to form nicotinic acid adenine dinucleotide (NaAD), which in turn is amidated to form NAD+ (Preiss and Handler (1958) *J. Biol. Chem.* 233:488-492; Preiss and Handler (1958b) *J. Biol. Chem.* 233:493-50).

NAD+ was initially characterized as a co-enzyme for oxidoreductases. Though conversions between NAD+, NADH, NADP and NADPH would not be accompanied by a loss of total co-enzyme, it was discovered that NAD+ is also turned over in cells for unknown purposes (Maayan (1964) *Nature* 204:1169-1170). Sirtuin enzymes such as Sir2 of *S. cerevisiae* and its homologs deacetylate lysine residues with consumption of an equivalent of NAD+ and this activity is required for Sir2 function as a transcriptional silencer (Imai, et al. (2000) *Cold Spring Harb. Symp. Quant. Biol.* 65:297-302). $NAD^+$-dependent deacetylation reactions are required not only for alterations in gene expression but also for repression of ribosomal DNA recombination and extension of lifespan in response to calorie restriction (Lin, et al. (2000) *Science* 289:2126-2128; Lin, et al. (2002) *Nature* 418:344-348). NAD+ is consumed by Sir2 to produce a mixture of 2'-and 3' O-acetylated ADP-ribose plus nicotinamide and the deacetylated polypeptide (Sauve, et al. (2001) *Biochemistry* 40:15456-15463). Additional enzymes, including poly(ADPribose) polymerases and cADPribose synthases are also $NAD^+$-dependent and produce nicotinamide and ADPribosyl products (Ziegler (2000) *Eur. J. Biochem.* 267:1550-1564; Burkle (2001) *Bioessays* 23:795-806).

The non-coenzymatic properties of NAD+ has renewed interest in NAD+ biosynthesis. Four recent publications have suggested what is considered to be all of the gene products and pathways to NAD+ in *S. cerevisiae* (Panozzo, et al. (2002) *FEBS Lett.* 517:97-102; Sandmeier, et al. (2002) *Genetics* 160:877-889; Bitterman, et al. (2002) J. Biol. Chem. 277:45099-45107; Anderson, et al. (2003) *Nature* 423:181-185) depicting convergence of the flux to NAD+ from de novo synthesis, nicotinic acid import, and nicotinamide salvage at NaMN (Scheme 1).

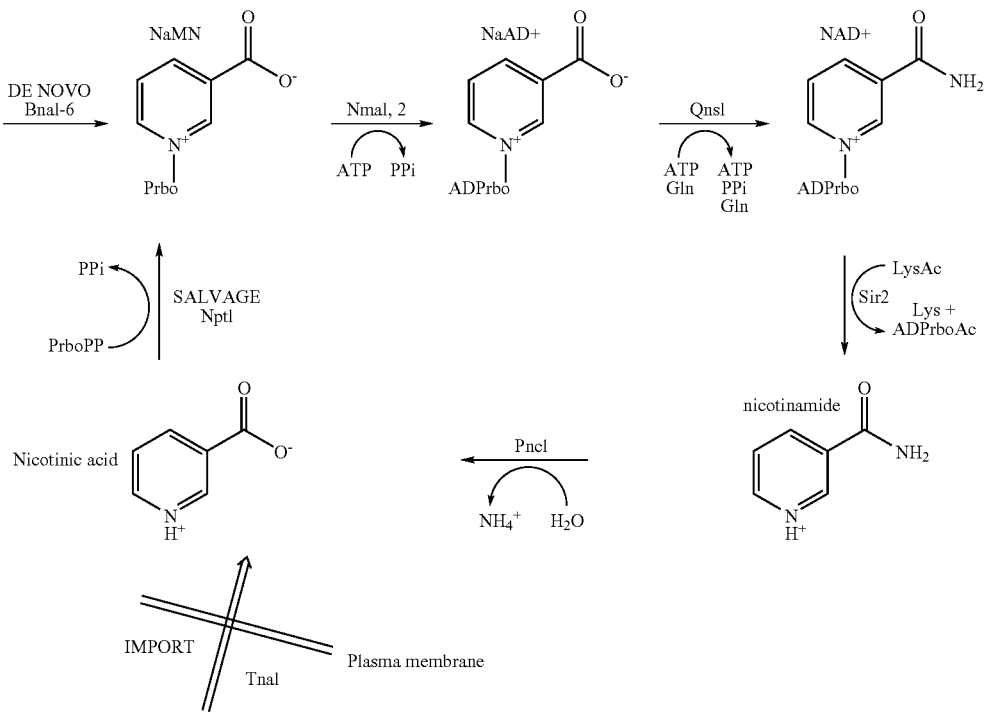

Scheme 1

SUMMARY OF THE INVENTION

It has now been shown that nicotinamide riboside, which was known to be an NAD+ precursor in bacteria such as *Haemophilus influenza* (Gingrich and Schlenk (1944) *J. Bacteriol.* 47:535-550; Leder and Handler (1951) *J. Biol. Chem.* 189:889-899; Shifrine and Biberstein (1960) *Nature* 187: 623) that lack the enzymes of the de novo and Preiss-Handler pathways (Fleischmann, et al. (1995) *Science* 269:496-512), is an NAD+ precursor in a previously unknown but conserved eukaryotic NAD+ biosynthetic pathway. Yeast nicotinamide riboside kinase, Nrk1, and human Nrk enzymes with specific functions in NAD+ metabolism are provided herein. The specificity of these enzymes indicates that they are the long-sought tiazofurin kinases that perform the first step in converting cancer drugs such as tiazofurin and benzamide riboside and their analogs into toxic NAD+ analogs. Further, yeast mutants of defined genotype were used to identify sources of nicotinamide riboside and it is shown that milk is a source of nicotinamide riboside.

Accordingly, the present invention is an isolated nucleic acid encoding a eukaryotic nicotinamide riboside kinase polypeptide. A eukaryotic nicotinamide riboside kinase nucleic acid encompasses (a) a nucleotide sequence of SEQ ID NO:1, SEQ ID NO:2 or SEQ ID NO:3; (b) a nucleotide sequence that hybridizes to a nucleotide sequence of SEQ ID NO:1, SEQ ID NO:2 or SEQ ID NO:3 or its complementary nucleotide sequence under stringent conditions, wherein said nucleotide sequence encodes a functional nicotinamide riboside kinase polypeptide; or (c) a nucleotide sequence encoding an amino acid sequence encoded by the nucleotide sequences of (a) or (b), but which has a different nucleotide sequence than the nucleotide sequences of (a) or (b) due to the degeneracy of the genetic code or the presence of non-translated nucleotide sequences.

The present invention is also an expression vector containing an isolated nucleic acid encoding a eukaryotic nicotinamide riboside kinase polypeptide. In one embodiment, the expression vector is part of a composition containing a pharmaceutically acceptable carrier. In another embodiment, the composition further contains a prodrug wherein the prodrug is a nicotinamide riboside-related analog that is phosphorylated by the expressed nicotinamide riboside kinase thereby performing the first step in activating said prodrug.

The present invention is also an isolated eukaryotic nicotinamide riboside kinase polypeptide. In one embodiment, the isolated nicotinamide riboside kinase polypeptide has an amino acid sequence having at least about 70% amino acid sequence similarity to an amino acid sequence of SEQ ID NO:4, SEQ ID NO:5 or SEQ ID NO:6 or a functional fragment thereof.

The present invention is further a cultured cell containing an isolated nucleic acid encoding a eukaryotic nicotinamide riboside kinase polypeptide or a polypeptide encoded thereby.

Still further, the present invention is a composition containing an isolated eukaryotic nicotinamide riboside kinase polypeptide and a pharmaceutically acceptable carrier. In one embodiment, the composition further contains a prodrug wherein said prodrug is a nicotinamide riboside-related analog that is phosphorylated by the nicotinamide riboside kinase thereby performing the first step in activating said prodrug.

The present invention is also a method for treating cancer by administering to a patient having or suspected of having cancer an effective amount of a nicotinamide riboside-related prodrug in combination with an isolated eukaryotic nicotinamide riboside kinase polypeptide or expression vector containing an isolated nucleic acid sequence encoding an eukaryotic nicotinamide riboside kinase polypeptide wherein the nicotinamide riboside kinase polypeptide phosphorylates the prodrug thereby performing the first step in activating the prodrug so that the signs or symptoms of said cancer are decreased or eliminated.

The present invention is further a method for identifying a natural or synthetic source for nicotinamide riboside. The method involves contacting a first cell lacking a functional glutamine-dependent NAD+ synthetase with an isolated extract from a natural source or synthetic; contacting a second cell lacking functional glutamine-dependent NAD+ synthetase and nicotinamide riboside kinase with the isolated extract; and detecting growth of the first cell compared to the growth of the second cell, wherein the presence of growth in the first cell and absence of growth in the second cell is indicative of the presence of nicotinamide riboside in the isolated extract. In one embodiment, the natural source is cow's milk.

Further, the present invention is a dietary supplement composition containing nicotinamide riboside identified in accordance with the methods of the present invention and a carrier.

Moreover, the present invention is a method for preventing or treating a disease or condition associated with the nicotinamide riboside kinase pathway of NAD+ biosynthesis. The method involves administering to a patient having a disease or condition associated with the nicotinamide riboside kinase pathway of NAD+ biosynthesis an effective amount of a nicotinamide riboside composition so that the signs or symptoms of the disease or condition are prevented or reduced. In one embodiment, the nicotinamide riboside is neuroprotective. In another embodiment the nicotinamide riboside is anti-fungal. In a further embodiment, the nicotinamide riboside is administered in combination with tryptophan, nicotinic acid or nicotinamide.

The present invention is also an in vitro method for identifying a nicotinamide riboside-related prodrug. The method involves contacting a nicotinamide riboside kinase polypeptide with a nicotinamide riboside-related test agent and determining whether said test agent is phosphorylated by said nicotinamide riboside kinase polypeptide wherein phosphorylation of said test agent is indicative of said test agent being a nicotinamide riboside-related prodrug. A nicotinamide riboside-related prodrug identified by this method is also encompassed within the present invention.

The present invention is further a cell-based method for identifying a nicotinamide riboside-related prodrug. This method involves contacting a first test cell which expresses a recombinant Nrk polypeptide with a nicotinamide riboside-related test agent; contacting a second test cell which lacks a functional Nrk polypeptide with the same test agent; and determining the viability of the first and second test cells, wherein sensitivity of the first cell and not the second cell is indicative of a nicotinamide riboside-related prodrug. A nicotinamide riboside-related prodrug identified by this method is also encompassed within the context of the present invention.

The present invention is also a method for identifying an individual or tumor which is susceptible to treatment with a nicotinamide riboside-related prodrug. This method involves detecting the presence of mutations in, or the level of expression of, a nicotinamide riboside kinase in an individual or tumor wherein the presence of a mutation or change in expression of nicotinamide riboside kinase in said individual or tumor compared to a control is indicative of said individual or tumor having an altered level of susceptibility to treatment with a nicotinamide riboside-related prodrug.

BRIEF DESCRIPTION OF THE DRAWINGS

FIG. 1 shows the amino acid sequence alignment and consensus sequence (SEQ ID NO:34) of human Nrk1 (SEQ ID NO:5), human Nrk2 (SEQ ID NO:6), *S. cerevisiae* Nrk1 (SEQ ID NO:4), *S. pombe* nrk1 (SEQ ID NO:7), as compared to portions of *S. cerevisiae* uridine/cytidine kinase Urk1 (SEQ ID NO:8) and *E. coli* pantothenate kinase (SEQ ID NO:9).

DETAILED DESCRIPTION OF THE INVENTION

A *Saccharomyces cerevisiae* QNS1 gene encoding glutamine-dependent NAD+synthetase has been characterized and mutation of either the glutaminase active site or the NAD+ synthetase active site resulted in inviable cells (Bieganowski, et al. (2003) *J. Biol. Chem.* 278:33049-33055). Possession of strains containing the qns1 deletion and a plasmid-borne QNS1 gene allowed a determination of whether the canonical de novo, import and salvage pathways for NAD+ of Scheme 1 (Panozzo, et al. (2002) supra; Sandmeier, et al. (2002) supra; Bitterman, et al. (2002) supra; Anderson, et al. (2003) supra) are a complete representation of the metabolic pathways to NAD+ in *S. cerevisiae*. The pathways depicted in scheme 1 suggest that: nicotinamide is deamidated to nicotinic acid before the pyridine ring is salvaged to make more NAD+, thus supplementation with nicotinamide may not rescue qns1 mutants by shunting nicotinamide-containing precursors through the pathway; and QNS1 is common to the three pathways, thus there may be no NAD+ precursor that rescues qns1 mutants. However, it has now been found that while nicotinamide does not rescue qns1 mutants even at 1 or 10 mM, nicotinamide riboside functions as a vitamin form of NAD+ at 10 μM.

Anticancer agents such as tiazofurin (Cooney, et al. (1983) *Adv. Enzyme Regul.* 21:271-303) and benzamide riboside (Krohn, et al. (1992) *J. Med. Chem.* 35:511-517) have been shown to be metabolized intracellularly to NAD+ analogs, taizofurin adenine dinucleotide and benzamide adenine dinucleotide, which inhibit IMP dehydrogenase the rate-limiting enzyme for de novo purine nucleotide biosynthesis.

Though an NMN/NaMN adenylyltransferase is thought to be the enzyme that converts the mononucleotide intermediates to NAD+ analogs and the structural basis for this is known (Zhou et al. (2002) supra), several different enzymes including adenosine kinase, 5' nucleotidase (Fridland, et al. (1986) *Cancer Res.* 46:532-537; Saunders, et al. (1990) *Cancer Res.* 50:5269-5274) and a specific nicotinamide riboside kinase (Saunders, et al. (1990) supra) have been proposed to be responsible for tiazofurin phosphorylation in vivo. A putative nicotinamide riboside kinase (Nrk) activity was purified, however no amino acid sequence information was obtained and, as a consequence, no genetic test was performed to assess its function (Sasiak and Saunders (1996) *Arch. Biochem. Biophys.* 333:414-418).

Using a qns1 deletion strain that was additionally deleted for yeast homologs of candidate genes encoding nucleoside kinases proposed to phosphorylate tiazofurin, i.e., adenosine kinase ado1 (Lecoq, et al. (2001) *Yeast* 18:335-342), uridine/cytidine kinase urk1 (Kern (1990) *Nucleic Acids Res.* 18:5279; Kurtz, et al. (1999) *Curr. Genet.* 36:130-136), and ribokinase rbk1 (Thierry, et al. (1990) *Yeast* 6:521-534), it was determined whether the nucleoside kinases are uniquely or collectively responsible for utilization of nicotinamide riboside. It was found that despite these deletions, the strain retained the ability to utilize nicotinamide riboside in an anabolic pathway independent of NAD+ synthetase.

Given that mammalian pharmacology provided no useful clue to the identity of a putative fungal Nrk, it was considered whether the gene might have been conserved with the Nrk of *Haemophilus influenza*. The Nrk domain of *H. influenza* is encoded by amino acids 225 to 421 of the NadR gene product (the amino terminus of which is NMN adenylyltransferase). Though this domain is structurally similar to yeast thymidylate kinase (Singh, et al. (2002) *J. Biol. Chem.* 277:33291-33299), sensitive sequence searches revealed that bacterial Nrk has no ortholog in yeast. Genomic searches with the Nrk domain of *H. influenza* NadR have identified a growing list of bacterial genomes predicted to utilize nicotinamide riboside as an NAD+ precursor (Kurnasov, et al. (2002) *J. Bacteriol.* 184:6906-6917). Thus, had fungi possessed NadR Nrk-homologous domains, comparative genomics would have already predicted that yeast can salvage nicotinamide riboside.

To identify the Nrk of *S. cerevisiae*, an HPLC assay for the enzymatic activity was established and used in combination with a biochemical genomics approach to screen for the gene encoding this activity (Martzen, et al. (1999) *Science* 286: 1153-1155). Sixty-four pools of 90-96 *S. cerevisiae* open reading frames fused to glutathione S-transferase (GST), expressed in *S. cerevisiae*, were purified as GST fusions and screened for the ability to convert nicotinamide riboside plus ATP to NMN plus ADP. Whereas most pools contained activities that consumed some of the input ATP, only pool 37 consumed nicotinamide riboside and produced NMN. In pool 37, approximately half of the 1 mM ATP was converted to ADP and the 500 μM nicotinamide riboside peak was almost entirely converted to NMN. Examination of the 94 open reading frames that were used to generate pool 37 revealed that YNL129W (SEQ ID NO:1) encodes a predicted 240 amino acid polypeptide with a 187 amino acid segment containing 23% identity with the 501 amino acid yeast uridine/cytidine kinase Urk1 and remote similarity with a segment of *E. coli* pantothenate kinase panK (Yun, et al. (2000) *J. Biol. Chem.* 275:28093-28099) (FIG. 1). After cloning YNL129W into a bacterial expression vector it was ascertained whether this homolog of metabolite kinases was the eukaryotic Nrk. The specific activity of purified YNL129W was ~100-times that of pool 37, consistent with the idea that all the Nrk activity of pool 37 was encoded by this open reading frame. To test genetically whether this gene product phosphorylates nicotinamide riboside in vivo, a deletion of YNL129W was created in the qns1 background. It was found that nicotinamide riboside rescue of the qns1 deletion strain was entirely dependent on this gene product. Having shown biochemically and genetically that YNL129W encodes an authentic Nrk activity, the gene was designated NRK1.

A PSI-BLAST (Altschul, et al. (1997) *Nucleic Acids Res.* 25:3389-3402) comparison was conducted on the predicted *S. cerevisiae* Nrk1 polypeptide and an orthologous human protein Nrk1 (NP_060351; SEQ ID NO:5; FIG. 1) was found. The human NP_060351 protein encoded at locus 9q21.31 is a polypeptide of 199 amino acids and is annotated as an uncharacterized protein of the uridine kinase family. In addition, a second human gene product Nrk2 (NP_733778; SEQ ID NO:6; FIG. 1) was found that is 57% identical to human Nrk1. Nrk2 is a 230 amino acid splice form of what was described as a 186 amino acid muscle integrin beta 1 binding protein (ITGB1BP3) encoded at 19p13.3 (Li, et al. (1999) *J. Cell Biol.* 147:1391-1398; Li, et al. (2003) *Dev. Biol.* 261:209-219). Amino acid conservation between *S. cerevisiae, S. pombe* and human Nrk homologs and similarity with fragments of *S. cerevisiae* Urk1 and *E. coli* panK is shown in FIG. 1. Fungal and human Nrk enzymes are members of a metabolite kinase superfamily that includes pantothenate kinase but is unrelated to bacterial nicotinamide riboside kinase. Robust complementation of the failure of qns1 nrk1 to grow on nicotinamide riboside-supplemented media was provided by human NRK1 and human NRK2 cDNA even when expressed from the GAL1 promoter on glucose.

As shown in Table 1, purification of yeast Nrk1 and human Nrk1 and Nrk2 revealed high specificity for phosphorylation of nicotinamide riboside and tiazofurin.

TABLE 1

|  | Nicotinamide riboside | Tiazofurin | Uridine | Cytidine |
|---|---|---|---|---|
| Human Nrk1 | 275 ± 17 | 538 ± 27 | 19.3 ± 1.7 | 35.5 ± 6.4 |
| Human Nrk2 | 2320 ± 20 | 2150 ± 210 | 2220 ± 170 | 222 ± 8 |
| Yeast Nrk1 | 535 ± 60 | 1129 ± 134 | 15.2 ± 3.4 | 82.9 ± 4.4 |

Specific activity is expressed in nmole mg$^{-1}$ min$^{-1}$ for phosphorylation of nucleoside substrates.

In the cases of yeast and human Nrk1 enzymes, the enzymes preferred tiazofurin to the natural substrate nicotinamide riboside by a factor of two and both enzymes retained less than 7% of their maximal specific activity on uridine and cytidine. In the case of human Nrk2, the 230 amino acid form was essentially equally active on nicotinamide riboside, tiazofurin and uridine with less than 10% of corresponding activity on cytidine. Conversely, the 186 amino acid integrin beta 1 binding protein form was devoid of enzymatic activity in this in vitro assay and was not functional as an Nrk in vivo. However, both the 186 and 230 amino acid isoforms function in vivo in a yeast nicotinamide riboside utilization assay. Thus, though Nrk2 may contribute additionally to formation of uridylate, these data demonstrate that fungi and mammals possess specific nicotinamide riboside kinases that function to synthesize NAD+ through NMN in addition to the well-known pathways through NaMN. Identification of Nrk enzymatic activities thus accounts for the dual specificity of fungal and mammalian NaMN/NMN adenylyltransferases.

On the basis of SAGE data, NRK1 is a rare message in many tissues examined while NRK2 is highly expressed in heart and skeletal muscle and has lower level expression in retinal epithelium and placenta (Boon, et al. (2002) *Proc. Natl. Acad. Sci. USA* 99:11287-11292). From cancer cell line to cancer cell line the expression levels are quite variable (Boon, et al. (2002) supra). Thus, in individuals whose tumors are NRK1, NRK2-low, tiazofurin conversion to NAD+ may occur more extensively in the patients hearts and muscles than in tumors. In tumors that are NRK1 and/or NRK2-high, a substantial amount of tiazofurin may be converted to tiazofurin adenine dinucleotide in tumors.

A yeast qns1 mutant was used to screen for natural sources of nicotinamide riboside wherein it was identified in an acid whey preparation of cowls milk. Unlike the original screen for vitamins in protein-depleted extracts of liver for reversal of black-tongue in starving dogs (Elvehjem, et al. (1938) *J. Biol. Chem.* 123:137-149), this assay is pathway-specific in identifying NAD+ precursors. Because of the qns1 deletion, nicotinic acid and nicotinamide do not score positively in this assay. As the factor from milk requires nicotinamide riboside kinase for growth, the nutrient is clearly nicotinamide riboside and not NMN or NAD+.

A revised metabolic scheme for NAD+, incorporating Nrk1 homologs and the nicotinamide riboside salvage pathway is shown in Scheme 2 wherein double arrows depict metabolic steps common to yeast and humans (with yeast gene names) and single arrows depict steps unique to humans (PBEF, nicotinamide phosphoribosyltransferase) and yeast (Pnc1, nicotinamidase).

Scheme 2

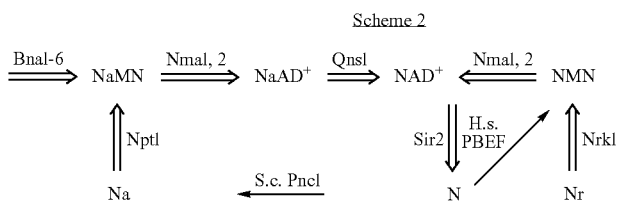

A difference between humans and yeasts concerns the organisms' uses of nicotinamide and nicotinic acid, the two niacins that were co-identified as anti-black tongue factor (Elvehjem, et al. (1938) supra). Humans encode a homolog of the *Haemophilus ducreyi* nadV gene, termed pre-B-cell colony enhancing factor, that may convert nicotinamide to NMN (Rongvaux, et al. (2002) *Eur. J. Immunol.* 32:3225-3234) and is highly induced during lymphocyte activation (Samal, et al. (1994) *Mol. Cell. Biol.* 14:1431-1437). In contrast, *S. cerevisiae* lacks a homolog of nadV and instead has a homolog of the *E. coli* pncA gene, termed PNC1, that converts nicotinamide to nicotinic acid for entry into the Preiss-Handler pathway (Ghislain, et al. (2002) *Yeast* 19:215-224; Sandmeier, et al. (2002) supra). Though the Preiss-Handler pathway is frequently considered a salvage pathway from nicotinamide, it technically refers to the steps from nicotinic acid to NAD+ (Preiss and Handler (1958) supra; Preiss and Handler (1958) supra). Reports that nicotinamidase had been purified from mammalian liver in the 1960s (Petrack, et al. (1965) *J. Biol. Chem.* 240:1725-1730) may have contributed to the sense that fungal and animal NAD+ biosynthesis is entirely conserved. However, animal genes for nicotinamidase have not been identified and there is no compelling evidence that nicotinamide and nicotinic acid are utilized as NAD+ precursors through the same route in mammals. The persistence of "niacin" as a mixture of nicotinamide and nicotinic acid may attest to the utility of utilizing multiple pathways to generate NAD+ and indicates that supplementation with nicotinamide riboside as third importable NAD+ precursor can be beneficial for certain conditions.

First reported in 1955, high doses of nicotinic acid are effective at reducing cholesterol levels (Altschul, et al. (1955) *Arch. Biochem. Biophys.* 54:558-559). Since the initial report, many controlled clinical studies have shown that nicotinic acid preparations, alone and in combination with HMG CoA reductase inhibitors, are effective in controlling low-density lipoprotein cholesterol, increasing high-density lipoprotein cholesterol, and reducing triglyceride and lipoprotein a levels in humans (Pasternak, et al. (1996) *Ann. Intern. Med.* 125:529-540). Though nicotinic acid treatment effects all of the key lipids in the desirable direction and has been shown to reduce mortality in target populations (Pasternak, et al. (1996) supra), its use is limited because of a side effect of heat and redness termed "flushing," which is significantly effected by the nature of formulation (Capuzzi, et al. (2000) *Curr. Atheroscler. Rep.* 2:64-71). Thus, nicotinamide riboside supplementation could be one route to improve lipid profiles in humans. Further, nicotinamide is protective in animal models of stroke (Klaidman, et al. (2003) *Pharmacology* 69:150-157) and nicotinamide riboside could be an important supplement for acute conditions such as stroke. Additionally, regulation of NAD+ biosynthetic enzymes could be useful in sensitizing tumors to compounds such as tiazofurin, to protect normal tissues from the toxicity of compounds such as tiazofurin adenine dinucleotide, and to stratify patients for the most judicious use of tiazofurin chemotherapy.

The present invention is an isolated nucleic acid containing a eukaryotic nucleotide sequence encoding a nicotinamide riboside kinase polypeptide. As used herein, an isolated molecule (e.g., an isolated nucleic acid such as genomic DNA, RNA or cDNA or an isolated polypeptide) means a molecule separated or substantially free from at least some of the other components of the naturally occurring organism, such as for example, the cell structural components or other polypeptides or nucleic acids commonly found associated with the molecule. When the isolated molecule is a polypeptide, said polypeptide is at least about 25%, 50%, 60%, 70%, 75%, 80%, 85%, 90%, 95%, 97%, 98%, 99% or more pure (w/w).

In one embodiment, the eukaryotic nucleotide sequence encoding a nicotinamide riboside kinase polypeptide is a nucleotide sequence of SEQ ID NO:1, SEQ ID NO:2 or SEQ ID NO:3. In another embodiment, the eukaryotic nucleotide sequence encoding a nicotinamide riboside kinase polypeptide is a nucleotide sequence that hybridizes to a nucleotide sequence of SEQ ID NO:1, SEQ ID NO:2 or SEQ ID NO:3 or its complementary nucleotide sequence under stringent conditions, wherein said nucleotide sequence encodes a functional nicotinamide riboside kinase polypeptide. In a further embodiment, the eukaryotic nucleotide sequence encoding a nicotinamide riboside kinase polypeptide is a nucleotide sequence encoding a functional nicotinamide riboside kinase polypeptide but which has a different nucleotide sequence than the nucleotide sequences of SEQ ID NO:1, SEQ ID NO:2, or SEQ ID NO:3 due to the degeneracy of the genetic code or the presence of non-translated nucleotide sequences.

As used herein, a functional polypeptide is one that retains at least one biological activity normally associated with that polypeptide. Alternatively, a functional polypeptide retains all of the activities possessed by the unmodified peptide. By retains biological activity, it is meant that the polypeptide retains at least about 50%, 60%, 75%, 85%, 90%, 95%, 97%, 98%, 99%, or more, of the biological activity of the native polypeptide (and can even have a higher level of activity than the native polypeptide). A non-functional polypeptide is one that exhibits essentially no detectable biological activity normally associated with the polypeptide (e.g., at most, only an insignificant amount, e.g., less than about 10% or even 5%).

As used herein, the term polypeptide encompasses both peptides and proteins, unless indicated otherwise.

A nicotinamide riboside kinase polypeptide or Nrk protein as used herein, is intended to be construed broadly and encompasses an enzyme capable of phosphorylating nicotinamide riboside. The term nicotinamide riboside kinase or Nrk also includes modified (e.g., mutated) Nrk that retains biological function (i.e., have at least one biological activity of the native Nrk protein, e.g., phosphorylating nicotinamide riboside), functional Nrk fragments including truncated molecules, alternatively spliced isoforms (e.g., the alternatively spliced isoforms of human Nrk2), and functional Nrk fusion polypeptides (e.g., an Nrk-GST protein fusion or Nrk-His tagged protein).

Any Nrk polypeptide or Nrk-encoding nucleic acid known in the art can be used according to the present invention. The Nrk polypeptide or Nrk-encoding nucleic acid can be derived from yeast, fungal (e.g., *Saccharomyces cerevisiae, Saccharomyces pombe, Pichia* sp., *Neurospora* sp., and the like) plant, animal (e.g., insect, avian (e.g., chicken), or mammalian (e.g., rat, mouse, bovine, porcine, ovine, caprine, equine, feline, canine, lagomorph, simian, human and the like) sources.

Representative cDNA and amino acid sequences of a *S. cerevisiae* Nrk1 are shown in SEQ ID NO:1 and SEQ ID NO:4 (FIG. 1), respectively. Representative cDNA and amino acid sequences of a human Nrk1 are shown in SEQ ID NO:2 and SEQ ID NO:5 (FIG. 1), respectively. Representative cDNA and amino acid sequences of a human Nrk2 are shown in SEQ ID NO:3 and SEQ ID NO:6 (FIG. 1), respectively. Other Nrk sequences encompassed by the present invention include, but are not limited to, Nrk1 of GENBANK accession numbers NM_017881, AK000566, BC001366, BC036804, and BC026243 and Nrk2 of GENBANK accession number NM_170678. Moreover, locus CAG61927 from the *Candida glabrata* CBS138 genome project (Dujon, et al. (2004) *Nature* 430:35-44) is 54% identical to the *Saccharomyces cerevisiae* Nrk1 protein. Particular embodiments of the present invention embrace a Nrk polypeptide having the conserved amino acid sequence XXXXDDFXK (SEQ ID NO:34), wherein $Xaa_1$ and $Xaa_2$ are aliphatic amino acid residues, $Xaa_3$ is His or Ser, $Xaa_4$ is a hydrophilic amino acid residue, and $Xaa_5$ is an aromatic amino acid residue.

To illustrate, hybridization of such sequences can be carried out under conditions of reduced stringency, medium stringency or even stringent conditions (e.g., conditions represented by a wash stringency of 35-40% Formamide with 5×Denhardt's solution, 0.5% SDS and 1×SSPE at 37° C.; conditions represented by a wash stringency of 40-45% Formamide with 5×Denhardt's solution, 0.5% SDS, and 1×SSPE at 42° C.; and/or conditions represented by a wash stringency of 50% Formamide with 5×Denhardt's solution, 0.5% SDS and 1×SSPE at 42° C., respectively) to the sequences specifically disclosed herein. See, e.g., Sambrook et al., *Molecular Cloning, A Laboratory Manual* (2d Ed. 1989) (Cold Spring Harbor Laboratory).

Alternatively stated, isolated nucleic acids encoding Nrk of the invention have at least about 50%, 60%, 70%, 80%, 90%, 95%, 97%, 98% or higher sequence similarity with the isolated nucleic acid sequences specifically disclosed herein (or fragments thereof, as defined above) and encode a functional Nrk as defined herein.

It will be appreciated by those skilled in the art that there can be variability in the nucleic acids that encode the Nrk of the present invention due to the degeneracy of the genetic code. The degeneracy of the genetic code, which allows different nucleic acid sequences to code for the same polypeptide, is well known in the literature (see Table 2).

TABLE 2

| Amino Acid | 3-Letter Code | 1-Letter Code | Codons |
|---|---|---|---|
| Alanine | Ala | A | GCA GCC GCG GCT |
| Cysteine | Cys | C | TGC TGT |
| Aspartic acid | Asp | D | GAC GAT |
| Glutamic acid | Glu | E | GAA GAG |
| Phenylalanine | Phe | F | TTC TTT |
| Glycine | Gly | G | GGA GGC GGG GGT |
| Histidine | His | H | CAC CAT |
| Isoleucine | Ile | I | ATA ATC ATT |
| Lysine | Lys | K | AAA AAG |
| Leucine | Leu | L | TTA TTG CTA CTC CTG CTT |
| Methionine | Met | M | ATG |
| Asparagine | Asn | N | AAC AAT |
| Proline | Pro | P | CCA CCC CCG CCT |
| Glutamine | Gln | Q | CAA CAG |
| Arginine | Arg | R | AGA AGG CGA CGC CGG CGT |
| Serine | Ser | S | AGC ACT TCA TCC TCG TCT |
| Threonine | Thr | T | ACA ACC ACG ACT |
| Valine | Val | V | GTA GTC GTG GTT |
| Tryptophan | Trp | W | TGG |
| Tyrosine | Tyr | Y | TAC TAT |

Further variation in the nucleic acid sequence can be introduced by the presence (or absence) of non-translated sequences, such as intronic sequences and 5' and 3' untranslated sequences.

Moreover, the isolated nucleic acids of the invention encompass those nucleic acids encoding Nrk polypeptides that have at least about 60%, 70%, 80%, 90%, 95%, 97%, 98% or higher amino acid sequence similarity with the polypeptide sequences specifically disclosed herein (or fragments thereof) and further encode a functional Nrk as defined herein.

As is known in the art, a number of different programs can be used to identify whether a nucleic acid or polypeptide has sequence identity or similarity to a known sequence. Sequence identity and/or similarity can be determined using standard techniques known in the art, including, but not limited to, the local sequence identity algorithm of Smith & Waterman (1981) *Adv. Appl. Math.* 2:482, by the sequence identity alignment algorithm of Needleman & Wunsch (1970) *J. Mol. Biol.* 48:443, by the search for similarity method of Pearson & Lipman (1988) *Proc. Natl. Acad. Sci. USA* 85:2444, by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux, et al. (1984) *Nucl. Acid Res.* 12:387-395, either using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle (1987) *J. Mol. Evol.* 35:351-360; the method is similar to that described by Higgins & Sharp (1989) *CABIOS* 5:151-153.

Another example of a useful algorithm is the BLAST algorithm, described in Altschul, et al. (1990) *J. Mol. Biol.* 215: 403-410 and Karlin, et al. (1993) *Proc. Natl. Acad. Sci. USA* 90:5873-5787. A particularly useful BLAST program is the WU-BLAST-2 program which was obtained from Altschul, et al. (1996) *Methods in Enzymology*, 266:460-480; http://blast.wustl/edu/blast/README.html. WU-BLAST-2 uses several search parameters, which can be set to the default values. The parameters are dynamic values and are established by the program itself depending upon the composition of the particular sequence and composition of the particular database against which the sequence of interest is being searched; however, the values can be adjusted to increase sensitivity.

An additional useful algorithm is gapped BLAST as reported by Altschul, et al. (1997) *Nucleic Acids Res.* 25:3389-3402.

A percentage amino acid sequence identity value can be determined by the number of matching identical residues divided by the total number of residues of the longer sequence in the aligned region. The longer sequence is the one having the most actual residues in the aligned region (gaps introduced by WU-Blast-2 to maximize the alignment score are ignored).

The alignment can include the introduction of gaps in the sequences to be aligned. In addition, for sequences which contain either more or fewer amino acids than the polypeptides specifically disclosed herein, it is understood that in one embodiment, the percentage of sequence identity will be determined based on the number of identical amino acids in relation to the total number of amino acids. Thus, for example, sequence identity of sequences shorter than a sequence specifically disclosed herein, will be determined using the number of amino acids in the shorter sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described below for sequence similarity calculations. Percent sequence identity can be calculated, for example, by dividing the number of matching identical residues by the total number of residues of the shorter sequence in the aligned region and multiplying by 100. The longer sequence is the one having the most actual residues in the aligned region.

To modify Nrk amino acid sequences specifically disclosed herein or otherwise known in the art, amino acid substitutions can be based on any characteristic known in the art, including the relative similarity or differences of the amino acid side-chain substituents, for example, their hydrophobicity, hydrophilicity, charge, size, and the like. In particular embodiments, conservative substitutions (i.e., substitution with an amino acid residue having similar properties) are made in the amino acid sequence encoding Nrk.

In making amino acid substitutions, the hydropathic index of amino acids may be considered. The importance of the hydropathic amino acid index in conferring interactive biologic function on a protein is generally understood in the art (see, Kyte and Doolittle (1982) *J. Mol. Biol.* 157:105). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics (Kyte and Doolittle (1982) supra), and these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is also understood in the art that the substitution of amino acids can be made on the basis of hydrophilicity. U.S. Pat. No. 4,554,101 states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

Isolated nucleic acids of this invention include RNA, DNA (including cDNAs) and chimeras thereof. The isolated nucleic acids can further contain modified nucleotides or nucleotide analogs.

The isolated nucleic acids encoding Nrk can be associated with appropriate expression control sequences, e.g., transcription/translation control signals and polyadenylation signals.

It will be appreciated that a variety of promoter/enhancer elements can be used depending on the level and tissue-specific expression desired. The promoter can be constitutive or inducible (e.g., the metallothionein promoter or a hormone inducible promoter), depending on the pattern of expression desired. The promoter can be native or foreign and can be a natural or a synthetic sequence. By foreign, it is intended that the transcriptional initiation region is not found in the wild-type host into which the transcriptional initiation region is introduced. The promoter is chosen so that it will function in the target cell(s) of interest. In particular embodiments, the promoter functions in tumor cells or in cells that can be used to express nucleic acids encoding Nrk for the purposes of large-scale protein production. Likewise, the promoter can be specific for these cells and tissues (i.e., only show significant activity in the specific cell or tissue type).

To illustrate, an Nrk coding sequence can be operatively associated with a cytomegalovirus (CMV) major immediate-early promoter, an albumin promoter, an Elongation Factor 1-α (EF1-α) promoter, a PγK promoter, a MFG promoter, a Rous sarcoma virus promoter, or a glyceraldehyde-3-phosphate promoter.

Moreover, specific initiation signals are generally required for efficient translation of inserted protein coding sequences. These translational control sequences, which can include the ATG initiation codon and adjacent sequences, can be of a variety of origins, both natural and synthetic.

Nrk can be expressed not only directly, but also as a fusion protein with a heterologous polypeptide, i.e. a signal sequence for secretion and/or other polypeptide which will aid in the purification of Nrk. In one embodiment, the heterologous polypeptide has a specific cleavage site to remove the heterologous polypeptide from Nrk.

In general, a signal sequence can be a component of the vector and should be one that is recognized and processed (i.e., cleaved by a signal peptidase) by the host cell. For production in a prokaryote, a prokaryotic signal sequence from, for example, alkaline phosphatase, penicillinase, lpp, or heat-stable enterotoxin II leaders can be used. For yeast secretion, one can use, e.g., the yeast invertase, alpha factor, or acid phosphatase leaders, the *Candida albicans* glucoamylase leader (EP 362,179), or the like (see, for example WO 90/13646). In mammalian cell expression, signal sequences from secreted polypeptides of the same or related species, as well as viral secretory leaders, for example, the herpes simplex glycoprotein D signal can be used.

Other useful heterologous polypeptides which can be fused to Nrk include those which increase expression or solubility of the fusion protein or aid in the purification of the fusion protein by acting as a ligand in affinity purification. Typical fusion expression vectors include those exemplified herein as well as pMAL (New England Biolabs, Beverly, Mass.) and pRIT5 (Pharmacia, Piscataway, N.J.) which fuse maltose E binding protein or protein A, respectively, to the target recombinant protein.

The isolated nucleic acids encoding Nrk can be incorporated into a vector, e.g., for the purposes of cloning or other laboratory manipulations, recombinant protein production, or gene delivery. In particular embodiments, the vector is an expression vector. Exemplary vectors include bacterial artificial chromosomes, cosmids, yeast artificial chromosomes, phage, plasmids, lipid vectors and viral vectors. By the term express, expresses or expression of a nucleic acid coding sequence, in particular an Nrk coding sequence, it is meant that the sequence is transcribed, and optionally, translated. Typically, according to the present invention, transcription and translation of the coding sequence will result in production of Nrk polypeptide.

The methods of the present invention provide a means for delivering, and optionally expressing, nucleic acids encoding Nrk in a broad range of host cells, including both dividing and non-dividing cells in vitro (e.g., for large-scale recombinant protein production or for use in screening assays) or in vivo (e.g., for recombinant large-scale protein production, for creating an animal model for disease, or for therapeutic purposes). In embodiments of the invention, the nucleic acid can be expressed transiently in the target cell or the nucleic acid can be stably incorporated into the target cell, for example, by integration into the genome of the cell or by persistent expression from stably maintained episomes (e.g., derived from Epstein Barr Virus).

The isolated nucleic acids, vectors, methods and pharmaceutical formulations of the present invention find use in a method of administering a nucleic acid encoding Nrk to a subject. In this manner, Nrk can thus be produced in vivo in the subject. The subject can have a deficiency of Nrk, or the production of a foreign Nrk in the subject can impart some therapeutic effect. Pharmaceutical formulations and methods of delivering nucleic acids encoding Nrk for therapeutic purposes are described herein.

Alternatively, an isolated nucleic acid encoding Nrk can be administered to a subject so that the nucleic acid is expressed by the subject and Nrk is produced and purified therefrom, i.e., as a source of recombinant Nrk protein. According to this embodiment, the Nrk is secreted into the systemic circulation or into another body fluid (e.g., milk, lymph, spinal fluid, urine) that is easily collected and from which the Nrk can be further purified. As a further alternative, Nrk protein can be produced in avian species and deposited in, and conveniently isolated from, egg proteins.

Likewise, Nrk-encoding nucleic acids can be expressed transiently or stably in a cell culture system for the purpose of screening assays or for large-scale recombinant protein production. The cell can be a bacterial, protozoan, plant, yeast, fungus, or animal cell. In one embodiment, the cell is an animal cell (e.g., insect, avian or mammalian), and in another embodiment a mammalian cell (e.g., a fibroblast).

It will be apparent to those skilled in the art that any suitable vector can be used to deliver the isolated nucleic acids of this invention to the target cell(s) or subject of interest. The choice of delivery vector can be made based on a number of factors known in the art, including age and species of the target host, in vitro vs. in vivo delivery, level and persistence of expression desired, intended purpose (e.g., for therapy or drug screening), the target cell or organ, route of delivery, size of the isolated nucleic acid, safety concerns, and the like.

Suitable vectors include virus vectors (e.g., retrovirus, alphavirus; vaccinia virus; adenovirus, adeno-associated virus, or herpes simplex virus), lipid vectors, poly-lysine vectors, synthetic polyamino polymer vectors that are used with nucleic acid molecules, such as plasmids, and the like.

As used herein, the term viral vector or viral delivery vector can refer to a virus particle that functions as a nucleic acid delivery vehicle, and which contains the vector genome packaged within a virion. Alternatively, these terms can be used to refer to the vector genome when used as a nucleic acid delivery vehicle in the absence of the virion.

Protocols for producing recombinant viral vectors and for using viral vectors for nucleic acid delivery can be found in *Current Protocols in Molecular Biology*, Ausubel, F. M. et al. (eds.) Greene Publishing Associates, (1989) and other standard laboratory manuals (e.g., Vectors for Gene Therapy. In: *Current Protocols in Human Genetics*. John Wiley and Sons, Inc.: 1997).

Particular examples of viral vectors are those previously employed for the delivery of nucleic acids including, for example, retrovirus, adenovirus, AAV, herpes virus, and poxvirus vectors.

In certain embodiments of the present invention, the delivery vector is an adenovirus vector. The term adenovirus as used herein is intended to encompass all adenoviruses, including the Mastadenovirus and Aviadenovirus genera. To date, at least forty-seven human serotypes of adenoviruses have been identified (see, e.g., Fields, et al., Virology, volume 2, chapter 67 (3d ed., Lippincott-Raven Publishers). In one embodiment, the adenovirus is a human serogroup C adenovirus, in another embodiment the adenovirus is serotype 2 (Ad2) or serotype 5 (Ad5) or simian adenovirus such as AdC68.

Those skilled in the art will appreciate that vectors can be modified or targeted as described in Douglas, et al. (1996) *Nature Biotechnology* 14:1574 and U.S. Pat. Nos. 5,922,315; 5,770,442 and/or 5,712,136.

An adenovirus genome can be manipulated such that it encodes and expresses a nucleic acid of interest but is inactivated in terms of its ability to replicate in a normal lytic viral life cycle. See, for example, Berkner, et al. (1988) *BioTechniques* 6:616; Rosenfeld, et al. (1991) *Science* 252:431-434; and Rosenfeld et al. (1992) *Cell* 68:143-155.

Recombinant adenoviruses can be advantageous in certain circumstances in that they are not capable of infecting non-dividing cells and can be used to infect a wide variety of cell types, including epithelial cells. Furthermore, the virus particle is relatively stable and amenable to purification and concentration, and can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., as occurs with retroviral DNA). Moreover, the carrying capacity of the adenoviral genome for foreign DNA is large relative to other delivery vectors (Haj-Ahmand and Graham (1986) *J. Virol.* 57:267).

In particular embodiments, the adenovirus genome contains a deletion therein, so that at least one of the adenovirus genomic regions does not encode a functional protein. For example, an adenovirus vectors can have E1 genes and packaged using a cell that expresses the E1 proteins (e.g., 293 cells). The E3 region is also frequently deleted as well, as there is no need for complementation of this deletion. In addition, deletions in the E4, E2a, protein IX, and fiber protein regions have been described, e.g., by Armentano, et al. (1997) *J. Virology* 71:2408; Gao, et al. (1996) *J. Virology* 70:8934; Dedieu, et al. (1997) *J. Virology* 71:4626; Wang, et al. (1997) *Gene Therapy* 4:393; U.S. Pat. No. 5,882,877. In general, the deletions are selected to avoid toxicity to the packaging cell. Combinations of deletions that avoid toxicity or other deleterious effects on the host cell can be routinely selected by those skilled in the art.

Those skilled in the art will appreciate that typically, with the exception of the E3 genes, any deletions will need to be complemented in order to propagate (replicate and package) additional virus, e.g., by transcomplementation with a packaging cell.

The present invention can also be practiced with gutted adenovirus vectors (as that term is understood in the art, see e.g., Lieber, et al. (1996) *J. Virol.* 70:8944-60) in which essentially all of the adenovirus genomic sequences are deleted.

Adeno-associated viruses (AAV) have also been employed as nucleic acid delivery vectors. For a review, see Muzyczka et al. *Curr. Topics in Micro. and Immunol.* (1992) 158:97-129). AAV are among the few viruses that can integrate their DNA into non-dividing cells, and exhibit a high frequency of stable integration into human chromosome 19 (see, for example, Flotte, et al. (1992) *Am. J. Respir. Cell. Mol. Biol.* 7:349-356; Samulski, et al., (1989) *J Virol.* 63:3822-3828; McLaughlin, et al. (1989) *J. Virol.* 62:1963-1973). A variety of nucleic acids have been introduced into different cell types using AAV vectors (see, for example, Hermonat, et al. (1984) *Proc. Natl. Acad. Sci. USA* 81:6466-6470; Tratschin, et al. (1985) *Mol. Cell. Biol.* 4:2072-2081; Wondisford, et al. (1988) *Mol. Endocrinol.* 2:32-39; Tratschin, et al. (1984) *J. Virol.* 51:611-619; and Flotte, et al. (1993) *J. Biol. Chem.* 268:3781-3790).

Any suitable method known in the art can be used to produce AAV vectors expressing the nucleic acids encoding Nrk of this invention (see, e.g., U.S. Pat. Nos. 5,139,941; 5,858,775; 6,146,874 for illustrative methods). In one particular method, AAV stocks can be produced by co-transfection of a rep/cap vector encoding AAV packaging functions and the template encoding the AAV vDNA into human cells infected with the helper adenovirus (Samulski, et al. (1989) *J. Virology* 63:3822). The AAV rep and/or cap genes can alternatively be provided by a packaging cell that stably expresses the genes (see, e.g., Gao, et al. (1998) *Human Gene Therapy*

9:2353; Inoue, et al. (1998) *J. Virol.* 72:7024; U.S. Pat. No. 5,837,484; WO 98/27207; U.S. Pat. No. 5,658,785; WO 96/17947).

Another vector for use in the present invention is Herpes Simplex Virus (HSV). HSV can be modified for the delivery of nucleic acids to cells by producing a vector that exhibits only the latent function for long-term gene maintenance. HSV vectors are useful for nucleic acid delivery because they allow for a large DNA insert of up to or greater than 20 kilobases; they can be produced with extremely high titers; and they have been shown to express nucleic acids for a long period of time in the central nervous system as long as the lytic cycle does not occur.

In other particular embodiments of the present invention, the delivery vector of interest is a retrovirus. The development of specialized cell lines (termed packaging cells) which produce only replication-defective retroviruses has increased the utility of retroviruses for gene therapy, and defective retroviruses are characterized for use in gene transfer for gene therapy purposes (for a review, see Miller (1990) *Blood* 76:271). A replication-defective retrovirus can be packaged into virions which can be used to infect a target cell through the use of a helper virus by standard techniques.

In addition to viral transfer methods, such as those illustrated above, non-viral methods can also be employed. Many non-viral methods of nucleic acid transfer rely on normal mechanisms used by mammalian cells for the uptake and intracellular transport of macromolecules. In particular embodiments, non-viral nucleic acid delivery systems rely on endocytic pathways for the uptake of the nucleic acid molecule by the targeted cell. Exemplary nucleic acid delivery systems of this type include liposomal derived systems, polylysine conjugates, and artificial viral envelopes.

In particular embodiments, plasmid vectors are used in the practice of the present invention. Naked plasmids can be introduced into muscle cells by injection into the tissue. Expression can extend over many months, although the number of positive cells is typically low (Wolff, et al. (1989) *Science* 247:247). Cationic lipids have been demonstrated to aid in introduction of nucleic acids into some cells in culture (Felgner and Ringold (1989) *Nature* 337:387). Injection of cationic lipid plasmid DNA complexes into the circulation of mice has been shown to result in expression of the DNA in lung (Brigham, et al. (1989) *Am. J. Med. Sci.* 298:278). One advantage of plasmid DNA is that it can be introduced into non-replicating cells.

In a representative embodiment, a nucleic acid molecule (e.g., a plasmid) can be entrapped in a lipid particle bearing positive charges on its surface and, optionally, tagged with antibodies against cell-surface antigens of the target tissue (Mizuno, et al. (1992) *No Shinkei Geka* 20:547; WO 91/06309; Japanese patent application 1047381; and European patent publication EP-A-43075).

Liposomes that consist of amphiphilic cationic molecules are useful non-viral vectors for nucleic acid delivery in vitro and in vivo (reviewed in Crystal (1995) *Science* 270:404-410; Blaese, et al. (1995) *Cancer Gene Ther.* 2:291-297; Behr, et al. (1994) *Bioconjugate Chem.* 5:382-389; Remy, et al. (1994) *Bioconjugate Chem.* 5:647-654; and Gao, et al. (1995) *Gene Therapy* 2:710-722). The positively charged liposomes are believed to complex with negatively charged nucleic acids via electrostatic interactions to form lipid:nucleic acid complexes. The lipid:nucleic acid complexes have several advantages as nucleic acid transfer vectors. Unlike viral vectors, the lipid:nucleic acid complexes can be used to transfer expression cassettes of essentially unlimited size. Since the complexes lack proteins, they can evoke fewer immunogenic and inflammatory responses. Moreover, they cannot replicate or recombine to form an infectious agent and have low integration frequency. A number of publications have demonstrated that amphiphilic cationic lipids can mediate nucleic acid delivery in vivo and in vitro (Felgner, et al. (1987) *Proc. Natl. Acad. Sci. USA* 84:7413-17; Loeffler, et al. (1993) *Methods in Enzymology* 217:599-618; Felgner, et al. (1994) *J. Biol. Chem.* 269:2550-2561).

As indicated above, Nrk polypeptide can be produced in, and optionally purified from, cultured cells or organisms expressing a nucleic acid encoding Nrk for a variety of purposes (e.g., screening assays, large-scale protein production, therapeutic methods based on delivery of purified Nrk).

In particular embodiments, an isolated nucleic acid encoding Nrk can be introduced into a cultured cell, e.g., a cell of a primary or immortalized cell line for recombinant protein production. The recombinant cells can be used to produce the Nrk polypeptide, which is collected from the cells or cell culture medium. Likewise, recombinant protein can be produced in, and optionally purified from an organism (e.g., a microorganism, animal or plant) being used essentially as a bioreactor.

Generally, the isolated nucleic acid is incorporated into an expression vector (viral or nonviral as described herein). Expression vectors compatible with various host cells are well-known in the art and contain suitable elements for transcription and translation of nucleic acids. Typically, an expression vector contains an expression cassette, which includes, in the 5' to 3' direction, a promoter, a coding sequence encoding an Nrk operatively associated with the promoter, and, optionally, a termination sequence including a stop signal for RNA polymerase and a polyadenylation signal for polyadenylase.

Expression vectors can be designed for expression of polypeptides in prokaryotic or eukaryotic cells. For example, polypeptides can be expressed in bacterial cells such as *E. coli*, insect cells (e.g., in the baculovirus expression system), yeast cells or mammalian cells. Some suitable host cells are discussed further in Goeddel (1990) Gene Expression Technology: Methods in Enzymology 185, Academic Press, San Diego, Calif. Examples of vectors for expression in yeast *S. cerevisiae* include pYepSec1 (Baldari, et al. (1987) *EMBO J.* 6:229-234), pMFa (Kurjan and Herskowitz (1982) *Cell* 30:933-943), pJRY88 (Schultz, et al. (1987) *Gene* 54:113-123), and pYES2 (INVITROGEN Corporation, San Diego, Calif.). Baculovirus vectors available for expression of nucleic acids to produce proteins in cultured insect cells (e.g., Sf 9 cells) include the pAc series (Smith, et al. (1983) *Mol. Cell. Biol.* 3:2156-2165) and the pVL series (Lucklow and Summers (1989) *Virology* 170:31-39).

Examples of mammalian expression vectors include pCDM8 (Seed (1987) *Nature* 329:840) and pMT2PC (Kaufman, et al. (1987) *EMBO J.* 6:187-195). When used in mammalian cells, the expression vector's control functions are often provided by viral regulatory elements. For example, commonly used promoters are derived from polyoma, adenovirus 2, cytomegalovirus and Simian Virus 40.

In addition to the regulatory control sequences discussed herein, the recombinant expression vector can contain additional nucleotide sequences. For example, the recombinant expression vector can encode a selectable marker gene to identify host cells that have incorporated the vector.

Vectors can be introduced into prokaryotic or eukaryotic cells via conventional transformation or transfection techniques. As used herein, the terms transformation and transfection refer to a variety of art-recognized techniques for introducing foreign nucleic acids (e.g., DNA) into a host cell, including calcium phosphate or calcium chloride co-precipitation, DEAE-dextran-mediated transfection, lipofection, electroporation, microinjection, DNA-loaded liposomes, lipofectamine-DNA complexes, cell sonication, gene bombardment using high velocity microprojectiles, and viral-mediated transfection. Suitable methods for transforming or transfecting host cells can be found in Sambrook, et al. (Molecular Cloning: A Laboratory Manual, 2nd Edition, Cold Spring Harbor Laboratory press (1989)), and other laboratory manuals.

Often only a small fraction of cells (in particular, mammalian cells) integrate the foreign DNA into their genome. In order to identify and select these integrants, a nucleic acid that encodes a selectable marker (e.g., resistance to antibiotics) can be introduced into the host cells along with the nucleic acid of interest. In particular embodiments, selectable markers include those that confer resistance to drugs, such as G418, hygromycin and methotrexate. Nucleic acids encoding a selectable marker can be introduced into a host cell on the same vector as that comprising the nucleic acid of interest or can be introduced on a separate vector. Cells stably transfected with the introduced nucleic acid can be identified by drug selection (e.g., cells that have incorporated the selectable marker gene will survive, while the other cells die).

Recombinant proteins can also be produced in a transgenic plant in which the isolated nucleic acid encoding the protein is inserted into the nuclear or plastidic genome. Plant transformation is known as the art. See, in general, *Methods in Enzymology* Vol. 153 (Recombinant DNA Part D) 1987, Wu and Grossman Eds., Academic Press and European Patent Application EP 693554.

The present invention further provides cultured or recombinant cells containing the isolated nucleic acids encoding Nrk for use in the screening methods and large-scale protein production methods of the invention (e.g., Nrk is produced and collected from the cells and, optionally, purified). In one particular embodiment, the invention provides a cultured cell containing an isolated nucleic acid encoding Nrk as described above for use in a screening assay for identifying a nicotinamide riboside-related prodrug. Also provided is a cell in vivo produced by a method comprising administering an isolated nucleic acid encoding Nrk to a subject in a therapeutically effective amount.

For in vitro screening assays and therapeutic administration, Nrk polypeptides can be purified from cultured cells. Typically, the polypeptide is recovered from the culture medium as a secreted polypeptide, although it also can be recovered from host cell lysates when directly expressed without a secretory signal. When Nrk is expressed in a recombinant cell other than one of human origin, the Nrk is completely free of proteins or polypeptides of human origin. However, it is necessary to purify Nrk from recombinant cell proteins or polypeptides to obtain preparations that are substantially homogeneous as to Nrk. As a first step, the culture medium or lysate is centrifuged to remove particulate cell debris. The membrane and soluble protein fractions are then separated. The Nrk can then be purified from the soluble protein fraction. Nrk thereafter can then be purified from contaminant soluble proteins and polypeptides with, for example, the following suitable purification procedures: by fractionation on immunoaffinity or ion-exchange columns; ethanol precipitation; reverse phase HPLC; chromatography on silica or on a cation-exchange resin such as DEAE; chromatofocusing; SDS-PAGE; ammonium sulfate precipitation; gel filtration using, for example, SEPHADEX G-75; ligand affinity chromatography, and protein A SEPHAROSE columns to remove contaminants such as IgG.

As Nrk phosphorylates tiazofurin, thereby performing the first step in activating it, Nrk is a useful target for identifying compounds which upon phosphorylation by Nrk and subsequent adenylylation inhibit IMPDH. As it has been shown that inhibitors of the IMPDH enzyme function as anti-bovine viral diarrhoea virus agents (Stuyver, et al. (2002) *Antivir. Chem. Chemother.* 13(6):345-52); inhibitors of IMPDH block hepatitis B replicon colony-forming efficiency (Zhou, et al. (2003) *Virology* 310(2):333-42); and tiazofurin (Cooney, et al. (1983) *Adv. Enzyme Regul.* 21:271-303) and benzamide riboside (Krohn, et al. (1992) *J. Med. Chem.* 35:511-517), when activated, inhibit IMP dehydrogenase; it is contemplated by using Nrk and the nicotinamide riboside pathway for drug screening, anticancer and antiviral agents will be identified. Accordingly, the present invention provides methods for identifying a nicotinamide riboside-related prodrug. As used herein, a nicotinamide riboside-related prodrug is any analog of nicotinamide riboside (e.g., tiazofurin and benzamide riboside) that, when phosphorylated by Nrk, ultimately can result in cell death or antiviral activity.

In one embodiment, a nicotinamide riboside-related prodrug is identified in a cell-free assay using isolated Nrk polypeptide. The steps involved in a this screening assay of the invention include, isolating or purifying an Nrk polypeptide; contacting or adding at least one nicotinamide riboside-related test agent to a point of application, such as a well, in the plate containing the isolated Nrk and a suitable phosphate donor such as ATP, Mg-ATP, Mn-ATP, Mg-GTP or Mn-GTP; and determining whether said test agent is phosphorylated by said Nrk polypeptide wherein phosphorylation of said test agent is indicative of a nicotinamide riboside-related prodrug. The phosphate donor can be added with or after the agent and the assay can be carried out under suitable assay conditions for phosphorylation, such as those exemplified herein.

With respect to the cell-free assay, test agents can be synthesized or otherwise affixed to a solid substrate, such as plastic pins, glass slides, plastic wells, and the like. Further, isolated Nrk can be free in solution, affixed to a solid support, or expressed on a cell surface.

Alternatively, an Nrk fusion protein can be provided to facilitate binding of Nrk to a matrix. For example, glutathione-S-transferase fusion proteins can be adsorbed onto glutathione SEPHAROSE beads (Sigma Chemical, St. Louis, Mo.) or glutathione derivatized microtitre plates, which are then combined with the test agent, and the mixture incubated under conditions conducive to complex formation (e.g., at physiological conditions for salt and pH) and phosphorylation as described above.

In another embodiment, a nicotinamide riboside-related prodrug is identified in a cell-based assay. The steps involved in a this screening assay of the invention include, contacting a first test cell which expresses a recombinant Nrk polypeptide with a nicotinamide riboside-related test agent; contacting a second test cell which lacks a functional Nrk polypeptide with the same test agent; and determining the viability of the first and second test cells wherein sensitivity or cell death of the first cell and not the second cell is indicative of a nicotinamide riboside-related prodrug. While the cell-based assay can be carried out using any suitable cell including bacteria, yeast, insect cells (e.g., with a baculovirus expression system), avian cells, mammalian cells, or plant cells, in particular embodiments, the test cell is a mammalian cell. In a further embodiment, said cell lacks a functional endogenous Nrk (e.g., the endogenous Nrk has been deleted or mutated or the cell does not express an Nrk). Said first test cell is transformed or transfected with an expression vector containing an exogenous Nrk so that upon exposure to a test agent, viability of the transformed cell can be compared to a second test cell lacking any Nrk activity. Thus, it can be ascertained whether the test agent is being activated in an Nrk-dependent manner. Cells modified to express a recombinant Nrk can be transiently or stably transformed with the nucleic acid encoding Nrk. Stably transformed cells can be generated by stable integration into the genome of the organism or by expression from a stably maintained episome (e.g., Epstein Barr Virus derived episomes).

Suitable methods for determining cell viability are well-established in the art. One such method uses non-permeant dyes (e.g., propidium iodide, 7-Amino Actinomycin D) that do not enter cells with intact cell membranes or active cell metabolism. Cells with damaged plasma membranes or with impaired/no cell metabolism are unable to prevent the dye from entering the cell. Once inside the cell, the dyes bind to intracellular structures producing highly fluorescent adducts which identify the cells as non-viable. Alternatively, cell viability can be determined by assaying for active cell metabolism which results in the conversion of a non-fluorescent substrate into a highly fluorescent product (e.g., fluorescein diacetate).

The test cells of the screening method of the invention can be cultured under standard conditions of temperature, incubation time, optical density, plating density and media composition corresponding to the nutritional and physiological requirements of the cells. However, conditions for maintenance and growth of the test cell can be different from those for assaying candidate agents in the screening methods of the invention. Any techniques known in the art can be applied to establish the optimal conditions.

Screening assays of the invention can be performed in any format that allows rapid preparation and processing of multiple reactions such as in, for example, multi-well plates of the 96-well variety. Stock solutions of the agents as well as assay components are prepared manually and all subsequent pipetting, diluting, mixing, washing, incubating, sample readout and data collecting is done using commercially available robotic pipetting equipment, automated work stations, and analytical instruments for detecting the output of the assay.

In addition to the reagents provided above, a variety of other reagents can be included in the screening assays of the invention. These include reagents like salts, neutral proteins, e.g., albumin, detergents, etc. Also, reagents that otherwise improve the efficiency of the assay, such as protease inhibitors, nuclease inhibitors, anti-microbial agents, and the like can be used.

Screening assays can also be carried out in vivo in animals. Thus, the present invention provides a transgenic non-human animal containing an isolated nucleic acid encoding Nrk, which can be produced according to methods well-known in the art. The transgenic non-human animal can be any species, including avians and non-human mammals. IN accordance with the invention, suitable non-human mammals include mice, rats, rabbits, guinea pigs, goats, sheep, pigs and cattle. Mammalian models for cancer, bovine diarrhoea viral infection or hepatitis C viral infection can also be used.

A nucleic acid encoding Nrk is stably incorporated into cells within the transgenic animal (typically, by stable integration into the genome or by stably maintained episomal constructs). It is not necessary that every cell contain the transgene, and the animal can be a chimera of modified and unmodified cells, as long as a sufficient number of cells contain and express the Nrk transgene so that the animal is a useful screening tool (e.g., so that administration of test agents give rise to detectable cell death or anti-viral activity).

Methods of making transgenic animals are known in the art. DNA constructs can be introduced into the germ line of an avian or mammal to make a transgenic animal. For example, one or several copies of the construct can be incorporated into the genome of an embryo by standard transgenic techniques.

In an exemplary embodiment, a transgenic non-human animal is produced by introducing a transgene into the germ line of the non-human animal. Transgenes can be introduced into embryonal target cells at various developmental stages. Different methods are used depending on the stage of development of the embryonal target cell. The specific line(s) of any animal used should, if possible, be selected for general good health, good embryo yields, good pronuclear visibility in the embryo, and good reproductive fitness.

Introduction of the transgene into the embryo can be accomplished by any of a variety of means known in the art such as microinjection, electroporation, lipofection or a viral vector. For example, the transgene can be introduced into a mammal by microinjection of the construct into the pronuclei of the fertilized mammalian egg(s) to cause one or more copies of the construct to be retained in the cells of the developing mammal(s). Following introduction of the transgenic construct into the fertilized egg, the egg can be incubated in vitro for varying amounts of time, or reimplanted into the surrogate host, or both. One common method is to incubate the embryos in vitro for about 1-7 days, depending on the species, and then reimplant them into the surrogate host.

The progeny of the transgenically manipulated embryos can be tested for the presence of the construct (e.g., by Southern blot analysis) of a segment of tissue. An embryo having one or more copies of the exogenous cloned construct stably integrated into the genome can be used to establish a permanent transgenic animal line carrying the transgenically added construct.

Transgenically altered animals can be assayed after birth for the incorporation of the construct into the genome of the offspring. This can be done by hybridizing a probe corresponding to the DNA sequence coding for the polypeptide or a segment thereof onto chromosomal material from the progeny. Those progeny found to contain at least one copy of the construct in their genome are grown to maturity.

Methods of producing transgenic avians are also known in the art, see, e.g., U.S. Pat. No. 5,162,215.

Nicotinamide riboside-related test agents can be obtained from a wide variety of sources including libraries of synthetic or natural compounds. Such agents can include analogs or derivatives of nicotinamide riboside as well as tiazofurin and benzamide riboside and analogs or derivatives thereof.

Alternatively, the isolated Nrk polypeptide can be used to generate a crystal structure of Nrk and synthetic nicotinamide riboside analogs can be designed. Based on the crystal structure of $E.\ coli$ panK, Asp127 appears to play a key role in transition-state stabilization of the transferring phosphoryl group of a pantothenate kinase (Yun, et al. (2000) $J.\ Biol.\ Chem.$ 275:28093-28099). Accordingly, it is contemplated the corresponding Nrk mutant, e.g., NRK2-E100Q, can be used to generate a stable complex between an Nrk and a nucleotides (i.e., Nrk2-E100Q+nicotinamide riboside+ATP can be stable enough to crystallize). Alternatively, Nrk can produce a stable complex in the presence of an inhibitor such as an ATP-mimetic compound (e.g., AMP-PNHP and AMP-PCH$_2$P). For metabolite kinases, bisubstrate inhibitors have been very successfully employed. For example, thymidylate kinase, which performs the reaction, dTMP+ATP->dTDP+AMP, is strongly inhibited by dTppppA (Bone, et al. (1986)

J. Biol. Chem. 261:16410-16413) and crystal structures were obtained with this inhibitor (Lavie, et al. (1998) *Biochemistry* 37:3677-3686).

It has been shown that the best inhibitors typically contain one or two more phosphates than the two substrates combined (i.e., dTppppA is not as good a substrate as dTpppppA). On the basis of the same types of results with adenosine kinase (Bone, et al. (1986) supra), it is contemplated that NrppppA (i.e., an NAD+ analog with two extra phosphates) will be a better inhibitor than NrpppA (i.e., an NAD+ analog with an extra phosphate, or, indeed, nicotinamide riboside+App-NHp). NAD+ analogs with extra phosphates can be generated using standard enzymatic methods (see, e.g., Guranowski, et al. (1990) *FEBS Lett.* 271:215-218) optimized for making a wide variety of adenylylated dinucleoside polyphosphates (Fraga, et al. (2003) *FEBS Lett.* 543:37-41), namely reaction of Nrpp (nicotinamide riboside diphosphate) and Nrppp (nicotinamide riboside triphosphate) with firefly luciferase-AMP. The diphosphorylated form of NMN (Nrpp) is prepared with either uridylate kinase or cytidylate kinase (NMN+ATP->Nrpp). The triphosphorylated form of NMN (Nrppp) is subsequently prepared with nucleoside diphosphate kinase (Nrpp+ATP->Nrppp). The resulting inhibitors are then used in crystallization trials and/or are soaked into Nrk crystals.

Once the three-dimensional structure of Nrk is determined, a potential test agent can be examined through the use of computer modeling using a docking program such as GRAM, DOCK, or AUTODOCK (Dunbrack, et al. (1997) *Folding & Design* 2:27-42). This procedure can include computer fitting of potential agents to Nrk to ascertain how well the shape and the chemical structure of the potential ligand will interact with Nrk. Computer programs can also be employed to estimate the attraction, repulsion, and steric hindrance of the test agent. Generally the tighter the fit (e.g., the lower the steric hindrance, and/or the greater the attractive force) the better substrate the agent will be since these properties are consistent with a tighter binding constraint. Furthermore, the more specificity in the design of a potential test agent the more likely that the agent will not interfere with related mammalian proteins. This will minimize potential side-effects due to unwanted interactions with other proteins.

The invention is also a method of treating cancer in a patient, having or suspected of having cancer, with an isolated nucleic acid, delivery vector, or polypeptide of the invention in combination with a nicotinamide riboside-related prodrug. Administration of the nucleic acid, delivery vector, or polypeptide of the present invention to a human subject or an animal can be by any means known in the art for administering nucleic acids, vectors, or polypeptides. A patient, as used herein, is intended to include any mammal such as a human, agriculturally-important animal, pet or zoological animal. A patient having or suspected of having a cancer is a patient who exhibits signs or symptoms of a cancer or because of inheritance, environmental or natural reasons is suspected of having cancer. Nucleic acids encoding Nrk, vectors containing the same, or Nrk polypeptides can be administered to the subject in an amount effective to decrease, alleviate or eliminate the signs or symptoms of a cancer (e.g., tumor size, feelings of weakness, and pain perception). The amount of the agent required to achieve the desired outcome of decreasing, eliminating or alleviating a sign or symptom of a cancer will be dependent on the pharmaceutical composition of the agent, the patient and the condition of the patient, the mode of administration, the type of condition or disease being prevented or treated, age and species of the patient, the particular vector, and the nucleic acid to be delivered, and can be determined in a routine manner.

While the prodrug and the Nrk nucleic acid, delivery vector, or polypeptide can be delivered concomitantly, in an alternative embodiment the Nrk nucleic acid, delivery vector, or polypeptide is provided first, followed by administration of the prodrug to precondition the cells to generate the activated or toxic drug.

Types of cancers which can be treated in accordance with the method of the invention include, but are not limited to, pancreatic cancer, endometrial cancer, small cell and non-small cell cancer of the lung (including squamous, adenocarcinoma and large cell types), squamous cell cancer of the head and neck, bladder, ovarian, cervical, breast, renal, CNS, and colon cancers, myeloid and lymphocytic leukemia, lymphoma, hepatic tumors, medullary thyroid carcinoma, multiple myeloma, melanoma, retinoblastoma, and sarcomas of the soft tissue and bone.

Typically, with respect to viral vectors, at least about $10^3$ virus particles, at least about $10^5$ virus particles, at least about $10^7$ virus particles, at least about $10^9$ virus particles, at least about $10^{11}$ virus particles, at least about $10^{12}$ virus particles, or at least about $10^{13}$ virus particles are administered to the patient per treatment. Exemplary doses are virus titers of about $10^7$ to about $10^{15}$ particles, about $10^7$ to about $10^{14}$ particles, about $10^8$ to about $10^{13}$ particles, about $10^{10}$ to about $10^{15}$ particles, about $10^{11}$ to about $10^{15}$ particles, about $10^{12}$ to about $10^{14}$ particles, or about $10^{12}$ to about $10^{13}$ particles.

In particular embodiments of the invention, more than one administration (e.g., two, three, four, or more administrations) can be employed over a variety of time intervals (e.g., hourly, daily, weekly, monthly, etc.) to achieve therapeutic levels of nucleic acid expression.

Tiazofurin is a nucleoside analog initially synthesized to be a cytidine deaminase inhibitor. Tiazofurin was shown to be a prodrug that is converted by cellular enzymes to TAD, an analog of NAD+, that inhibits IMP dehydrogenase, the rate limiting enzyme in producing GTP and dGTP (Cooney, et al. (1983) supra). In phase I/II trials of acute leukemia, tiazofurin produced response rates as high as 85% and was granted orphan drug status for treatment of CML in accelerated phase or blast crisis. Treatment of cultured cells has shown that tiazofurin selectively kills cancer cells by induction of apoptosis: the activity has been attributed both to the increased dependence of actively replicating cells on dGTP and to the addiction of many transformed genotypes to signaling through low molecular weight G proteins (Jayaram, et al. (2002) *Curr. Med. Chem.* 9:787-792). Examination of the sensitivity of the NCI-60 panel of cancer cell lines and the literature on tiazofurin indicates that particular breast, renal, CNS, colon and non-small cell lung-derived tumors are among the most sensitive while others from the same organ sites are among the most resistant (Johnson, et al. (2001) *Br. J. Cancer* 84:1424-1431). As was demonstrated herein, the function of nicotinamide riboside as an NAD+ precursor is entirely dependent on Nrk1 and human Nrks have at least as high specific activity in tiazofurin phosphorylation as in nicotinamide riboside phosphorylation. Because Nrk2 expression is muscle-specific (Li, et al. (1999) supra), and Nrk1 is expressed at a very low level (Boon, et al. (2002) supra), while NMN/NaMNAT is not restricted, it is contemplated that stratification of tumors by Nrk gene expression will largely predict and account for tiazofurin sensitivity.

Accordingly, the present invention is further a method for identifying an individual or tumor which is susceptible to treatment with a nicotinamide riboside-related prodrug. In one embodiment, the level of Nrk protein in an individual or tumor is detected by binding of a Nrk-specific antibody in an immunoassay. In another embodiment, the level of Nrk enzyme activity is determined using, for example, the nicotinamide riboside phosphorylation assay disclosed herein. In another embodiment, the level of Nrk RNA transcript is determined using any number of well-known RNA-based assays for detecting levels of RNA. Once detected, the levels of Nrk are compared to a known standard. A change in the level of Nrk, as compared to the standard, is indicative of an altered level of susceptibility to treatment with a nicotinamide riboside-related prodrug. In a still further embodiment, mutations or polymorphisms in the Nrk gene can be identified which result in an altered level of susceptibility to treatment with a nicotinamide riboside-related prodrug.

Optimized treatments for cancer and other diseases with nicotinamide riboside-related prodrugs are directed toward cells with naturally high levels of an Nrk provided herein or toward cells which have been recombinantly engineered to express elevated levels of an Nrk. Safety, specificity and efficacy of these treatments can be modulated by supplementation with or restriction of the amounts of any of the NAD+ precursors, namely tryptophan, nicotinic acid, nicotinamide, or nicotinamide riboside.

For the detection of Nrk protein levels, antibodies which specifically recognize Nrk are generated. These antibodies can be either polyclonal or monoclonal. Moreover, such antibodies can be natural or partially or wholly synthetically produced. All fragments or derivatives thereof (e.g., Fab, Fab', F(ab')$_2$, scFv, Fv, or Fd fragments) which maintain the ability to specifically bind to and recognize Nrk are also included. The antibodies can be a member of any immunoglobulin class, including any of the human classes: IgG, IgM, IgA, IgD, and IgE.

The Nrk-specific antibodies can be generated using classical cloning and cell fusion techniques. See, for example, Kohler and Milstein (1975) *Nature* 256:495-497; Harlow and Lane (1988) Antibodies: A Laboratory Manual, Cold Spring Harbor Laboratory, New York. Alternatively, antibodies which specifically bind Nrk are derived by a phage display method. Methods of producing phage display antibodies are well-known in the art (e.g., Huse, et al. (1989) *Science* 246 (4935):1275-81).

Selection of Nrk-specific antibodies is based on binding affinity and can be determined by various well-known immunoassays including, enzyme-linked immunosorbent, immunodiffusion chemiluminescent, immunofluorescent, immunohistochemical, radioimmunoassay, agglutination, complement fixation, immunoelectrophoresis, and immunoprecipitation assays and the like which can be performed in vitro, in vivo or in situ. Such standard techniques are well-known to those of skill in the art (see, e.g., "Methods in Immunodiagnosis", 2nd Edition, Rose and Bigazzi, eds. John Wiley & Sons, 1980; Campbell et al., "Methods and Immunology", W.A. Benjamin, Inc., 1964; and Oellerich, M. (1984) *J. Clin. Chem. Clin. Biochem.* 22:895-904).

Once fully characterized for specificity, the antibodies can be used in diagnostic or predictive methods to evaluate the levels of Nrk in healthy and diseased tissues (i.e., tumors) via techniques such as ELISA, western blotting, or immunohistochemistry.

The general method for detecting levels of Nrk protein provides contacting a sample with an antibody which specifically binds Nrk, washing the sample to remove non-specific interactions, and detecting the antibody-antigen complex using any one of the immunoassays described above as well a number of well-known immunoassays used to detect and/or quantitate antigens (see, for example, Harlow and Lane (1988) supra). Such well-known immunoassays include antibody capture assays, antigen capture assays, and two-antibody sandwich assays.

For the detection of nucleic acid sequences encoding Nrk, either a DNA-based or RNA-based method can be employed. DNA-based methods for detecting mutations in an Nrk locus (i.e., frameshift mutations, point mutations, missense mutations, nonsense mutations, splice mutations, deletions or insertions of induced, natural or inherited origin) include, but are not limited to, DNA microarray technologies, oligonucleotide hybridization (mutant and wild-type), PCR-based sequencing, single-strand conformational polymorphism (SSCP) analysis, heteroduplex analysis (HET), PCR, or denaturing gradient gel electrophoresis. Mutations can appear, for example, as a dual base call on sequencing chromatograms. Potential mutations are confirmed by multiple, independent PCR reactions. Exemplary single nucleotide polymorphisms which can be identified in accordance with the diagnostic method of the invention include, but are not limited to, NCBI SNP Cluster ID Nos. rs3752955, rs1045882, rs11519, and rs3185880 for human Nrk1 and Cluster ID Nos. rs2304190, rs4807536, and rs1055767 for human Nrk2.

To detect the levels of RNA transcript encoding the Nrk, nucleic acids are isolated from cells of the individual or tumor, according to standard methodologies (e.g., Sambrook et al. (1989) *Molecular Cloning, a Laboratory Manual*, Cold Spring Harbor Laboratories, New York). The nucleic acid can be whole cell RNA or fractionated to Poly-A+. It may be desirable to convert the RNA to a complementary DNA (cDNA). Normally, the nucleic acid is amplified.

A variety of methods can be used to evaluate or quantitate the level of Nrk RNA transcript present in the nucleic acids isolated from an individual or tumor. For example, levels of Nrk RNA transcript can be evaluated using well-known methods such as northern blot analysis (see, e.g., Sambrook et al. (1989) *Molecular Cloning, a Laboratory Manual*, Cold Spring Harbor Laboratories, New York); oligonucleotide or cDNA fragment hybridization wherein the oligonucleotide or cDNA is configured in an array on a chip or wafer; real-time PCR analysis, or RT-PCR analysis.

Suitable primers, probes, or oligonucleotides useful for such detection methods can be generated by the skilled artisan from the Nrk nucleic acid sequences provided herein. The term primer, as defined herein, is meant to encompass any nucleic acid that is capable of priming the synthesis of a nascent nucleic acid in a template-dependent process. Typically, primers are oligonucleotides from ten to twenty base pairs in length, but longer sequences can be employed. Primers can be provided in double-stranded or single-stranded form. Probes are defined differently, although they can act as primers. Probes, while perhaps capable of priming, are designed for binding to the target DNA or RNA and need not be used in an amplification process. In one embodiment, the probes or primers are labeled with, for example, radioactive species ($^{32}$P, $^{14}$C, $^{35}$S, $^3$H, or other label) or a fluorophore (rhodamine, fluorescein). Depending on the application, the probes or primers can be used cold, i.e., unlabeled, and the RNA or cDNA molecules are labeled.

Depending on the format, detection can be performed by visual means (e.g., ethidium bromide staining of a gel). Alternatively, the detection can involve indirect identification of the product via chemiluminescence, radiolabel or fluorescent label or even via a system using electrical or thermal impulse signals (Bellus (1994) *J. Macromol. Sci. Pure Appl. Chem.* A311:1355-1376).

After detecting mutations in Nrk or the levels of Nrk present in an individual or tumor, said mutations or levels are compared with a known control or standard. A known control can be a statistically significant reference group of individuals that are susceptible or lack susceptibility to treatment with a nicotinamide riboside-related prodrug to provide diagnostic or predictive information pertaining to the individual or tumor upon which the analysis was conducted.

As described herein, nicotinamide riboside isolated from deproteinized whey fraction of cow's milk was sufficient to support NRK1-dependent growth in a qns1 mutant. Accordingly, mutant strains generated herein will be useful in identifying other natural or synthetic sources for nicotinamide riboside for use in dietary supplements. Thus, the present invention also encompasses is a method for identifying such natural or synthetic sources. As a first step of the method, a first cell lacking a functional glutamine-dependent NAD+ synthetase is contacted with an isolated extract from a natural or synthetic source. In one embodiment, the first cell is a qns1 mutant (i.e., having no NAD+ synthetase) carrying the QNS1 gene on a URA3 plasmid. While any cell can be used, in particular embodiments a yeast cell is used in this method of the invention. A qns1 mutant strain has normal growth on 5-fluoroorotic acid (i.e., cured of the URA3 QNS1 plasmid) as long as it is supplied with nicotinamide riboside.

As a second step of the method, a second cell lacking a functional glutamine-dependent NAD+ synthetase and a functional nicotinamide riboside kinase is contacted with the same isolated extract from the natural or synthetic source of the prior step. Using a qns1 and nrk1 double mutant, it was demonstrated herein that the NRK1 gene is necessary for growth on nicotinamide riboside: qns1 and nrk1 are synthetically lethal even with nicotinamide riboside. This deletion strain is useful in this screening assay of the invention as it allows one to distinguish between nicotinamide riboside, NMN and NAD+ as the effective nutrient.

As a subsequent step of the method, the growth of the first cell and second cell are compared. If the isolated extract contains a nicotinamide riboside, the first cell will grow and the second cell will not.

Synthetic sources of nicotinamide riboside can include any library of chemicals commercially available from most large chemical companies including Merck, Glaxo, Bristol Meyers Squibb, Monsanto/Searle, Eli Lilly and Pharmacia. Natural sources which can be tested for the presence of a nicotinamide riboside include, but are not limited to, cow's milk, serum, meats, eggs, fruit and cereals. Isolated extracts of the natural sources can be prepared using standard methods. For example, the natural source can be ground or homogenized in a buffered solution, centrifuged to remove cellular debris, and fractionated to remove salts, carbohydrates, polypeptides, nucleic acids, fats and the like before being tested on the mutants strains of the invention. Any source of nicotinamide riboside that scores positively in the assay of the invention can be further fractionated and confirmed by standard methods of HPLC and mass spectrometry.

Nicotinic acid is an effective agent in controlling low-density lipoprotein cholesterol, increasing high-density lipoprotein cholesterol, and reducing triglyceride and lipoprotein (a) levels in humans (see, e.g., Miller (2003) *Mayo Clin. Proc.* 78(6):735-42). Though nicotinic acid treatment effects all of the key lipids in the desirable direction and has been shown to reduce mortality in target populations, its use is limited because of a side effect of heat and redness termed flushing, which is significantly effected by the nature of formulation. Further, nicotinamide protects against stroke injury in model systems, due to multiple mechanisms including increasing mitochondrial NAD+ levels and inhibiting PARP (Klaidman, et al. (2003) *Pharmacology* 69(3):150-7). Altered levels of NAD+ precursors have been shown to effect the regulation of a number of genes and lifespan in yeast (Anderson, et al. (2003) *Nature* 423(6936):181-5).

NAD+ administration and NMN adenylyltransferase (Nmnat1) expression have also been shown to protect neurons from axonal degeneration (Araki, et al. (2004) *Science* 305: 1010-1013). Because nicotinamide riboside is a soluble, transportable nucleoside precursor of NAD+, nicotinamide riboside can be used to protect against axonopathies such as those that occur in Alzheimer's Disease, Parkinson's Disease and Multiple Sclerosis. Expression of the NRK1 or NRK2 genes, or direct administration of nicotinamide riboside or a stable nicotinamide riboside prodrug, could also protect against axonal degeneration.

NMN adenylyltransferase overexpression has been shown to protect neurons from the axonopathies that develop with ischemia and toxin exposure, including vincristine treatment (Araki, et al. (2004) *Science* 305:1010-1013). Vincristine is one of many chemotherapeutic agents whose use is limited by neurotoxicity. Thus, administration of nicotinamide riboside or an effective nicotinamide riboside prodrug derivative could be used to protect against neurotoxicity before, during or after cytotoxic chemotherapy.

Further, conversion of benign *Candida glabrata* to the adhesive, infective form is dependent upon the expression of EPA genes encoding adhesins whose expression is mediated by NAD+ limitation, which leads to defective Sir2-dependent silencing of these genes (Domergue, et al. (March 2005) *Science*, 10.1126/science.1108640). Treatment with nicotinic acid reduces expression of adhesins and increasing nicotinic acid in mouse chow reduces urinary tract infection by *Candida glabrata*. Thus, nicotinamide riboside can be used in the treatment of fungal infections, in particular, those of *Candida* species by preventing expression of adhesins.

Accordingly, agents (e.g., nicotinamide riboside) that work through the discovered nicotinamide riboside kinase pathway of NAD+ biosynthesis could have therapeutic value in improving plasma lipid profiles, preventing stroke, providing neuroprotection with chemotherapy treatment, treating fungal infections, preventing or reducing neurodegeneration, or in prolonging health and well-being. Thus, the present invention is further a method for preventing or treating a disease or condition associated with the nicotinamide riboside kinase pathway of NAD+ biosynthesis by administering an effective amount of a nicotinamide riboside composition. Diseases or conditions which typically have altered levels of NAD+ or NAD+ precursors or could benefit from increased NAD+ biosynthesis by treatment with nicotinamide riboside include, but are not limited to, lipid disorders (e.g., dyslipidemia, hypercholesterolaemia or hyperlipidemia), stroke, neurodegenerative diseases (e.g., Alzheimer's, Parkinsons and Multiple Sclerosis), neurotoxicity as observed with chemotherapies, *Candida glabrata* infection, and the general health declines associated with aging. Such diseases and conditions can be prevented or treated by supplementing a diet or a therapeutic treatment regime with a nicotinamide riboside composition.

The source of nicotinamide riboside can be from a natural or synthetic source identified by the method of the instant invention, or can be chemically synthesized using established methods (Tanimori (2002) *Bioorg. Med. Chem. Lett.* 12:1135-1137; Franchetti (2004) *Bioorg. Med. Chem. Lett.* 14:4655-4658). In addition, the nicotinamide riboside can be a derivative (e.g., L-valine or L-phenylalanine esters) of nicotinamide riboside. For example, an L-valyl (valine) ester on the 5' O of acyclovir (valacyclovir) improved the pharmacokinetic properties of the drug by promoting transport and allowing cellular delivery of the nucleoside after hydrolysis by an abundant butyryl esterase (Han, et al. (1998) *Pharm. Res.* 15:1382-1386; Kim, et al. (2003) *J. Biol. Chem.* 278: 25348-25356). Accordingly, the present invention also encompasses derivatives of nicotinamide riboside, in particular L-valine or L-phenylalanine esters of nicotinamide riboside, which are contemplated as having improved pharmacokinetic properties (e.g., transport and delivery). Such derivatives can be used alone or formulated with a pharmaceutically acceptable carrier as disclosed herein.

An effective amount of nicotinamide riboside is one which prevents, reduces, alleviates or eliminates the signs or symptoms of the disease or condition being prevented or treated and will vary with the disease or condition. Such signs or symptoms can be evaluated by the skilled clinician before and after treatment with the nicotinamide riboside to evaluate the effectiveness of the treatment regime and dosages can be adjusted accordingly.

As alterations of NAD+ metabolism may need to be optimized for particular conditions, it is contemplated that nicotinamide riboside treatments can further be used in combination with other NAD+ precursors, e.g., tryptophan, nicotinic acid and/or nicotinamide.

Polypeptides, nucleic acids, vectors, dietary supplements (i.e. nicotinamide riboside), and nicotinamide riboside-related prodrugs produced or identified in accordance with the methods of the invention can be conveniently used or administered in a composition containing the active agent in combination with a pharmaceutically acceptable carrier. Such compositions can be prepared by methods and contain carriers which are well-known in the art. A generally recognized compendium of such methods and ingredients is Remington: The Science and Practice of Pharmacy, Alfonso R. Gennaro, editor, 20th ed. Lippincott Williams & Wilkins: Philadelphia, Pa., 2000. A carrier, pharmaceutically acceptable carrier, or vehicle, such as a liquid or solid filler, diluent, excipient, or solvent encapsulating material, is involved in carrying or transporting the subject compound from one organ, or portion of the body, to another organ, or portion of the body. Each carrier must be acceptable in the sense of being compatible with the other ingredients of the formulation and not injurious to the patient.

Examples of materials which can serve as carriers include sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Polypeptides, nucleic acids, vectors, dietary supplements, and nicotinamide riboside-related prodrugs produced or identified in accordance with the methods of the invention, hereafter referred to as compounds, can be administered via any route include, but not limited to, oral, rectal, topical, buccal (e.g., sub-lingual), vaginal, parenteral (e.g., subcutaneous, intramuscular including skeletal muscle, cardiac muscle, diaphragm muscle and smooth muscle, intradermal, intravenous, intraperitoneal), topical (i.e., both skin and mucosal surfaces, including airway surfaces), intranasal, transdermal, intraarticular, intrathecal and inhalation administration, administration to the liver by intraportal delivery, as well as direct organ injection (e.g., into the liver, into the brain for delivery to the central nervous system). The most suitable route in any given case will depend on the nature and severity of the condition being treated and on the nature of the particular compound which is being used.

For injection, the carrier will typically be a liquid, such as sterile pyrogen-free water, pyrogen-free phosphate-buffered saline solution, bacteriostatic water, or Cremophor (BASF, Parsippany, N.J.). For other methods of administration, the carrier can be either solid or liquid.

For oral therapeutic administration, the compound can be combined with one or more carriers and used in the form of ingestible tablets, buccal tablets, troches, capsules, elixirs, suspensions, syrups, wafers, chewing gums, foods and the like. Such compositions and preparations should contain at least 0.1% of active compound. The percentage of the compound and preparations can, of course, be varied and can conveniently be between about 0.1 to about 100% of the weight of a given unit dosage form. The amount of active compound in such compositions is such that an effective dosage level will be obtained.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring. The above listing is merely representative and one skilled in the art could envision other binders, excipients, sweetening agents and the like. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac or sugar and the like.

A syrup or elixir can contain the active agent, sucrose or fructose as a sweetening agent, methyl and propylparabens as preservatives, a dye and flavoring such as cherry or orange flavor. Of course, any material used in preparing any unit dosage form should be substantially non-toxic in the amounts employed. In addition, the active compounds can be incorporated into sustained-release preparations and devices including, but not limited to, those relying on osmotic pressures to obtain a desired release profile.

Formulations of the present invention suitable for parenteral administration contain sterile aqueous and non-aqueous injection solutions of the compound, which preparations are generally isotonic with the blood of the intended recipient. These preparations can contain anti-oxidants, buffers, bacteriostats and solutes which render the formulation isotonic with the blood of the intended recipient. Aqueous and non-aqueous sterile suspensions can include suspending agents and thickening agents. The formulations can be presented in unit\dose or multi-dose containers, for example sealed ampoules and vials, and can be stored in a freeze-dried (lyophilized) condition requiring only the addition of the sterile liquid carrier, for example, saline or water-for-injection immediately prior to use.

Formulations suitable for topical application to the skin can take the form of an ointment, cream, lotion, paste, gel, spray, aerosol, or oil. Carriers which can be used include petroleum jelly, lanoline, polyethylene glycols, alcohols, transdermal enhancers, and combinations of two or more thereof.

Formulations suitable for transdermal administration can be presented as discrete patches adapted to remain in intimate contact with the epidermis of the recipient for a prolonged period of time. Formulations suitable for transdermal administration can also be delivered by iontophoresis (see, for example, *Pharmaceutical Research* 3 (6):318 (1986)) and typically take the form of an optionally buffered aqueous solution of the compound. Suitable formulations contain citrate or bis\tris buffer (pH 6) or ethanol/water and contain from 0.1 to 0.2 M of the compound.

A compound can alternatively be formulated for nasal administration or otherwise administered to the lungs of a subject by any suitable means. In particular embodiments, the compound is administered by an aerosol suspension of respirable particles containing the compound, which the subject inhales. The respirable particles can be liquid or solid. The term aerosol includes any gas-borne suspended phase, which is capable of being inhaled into the bronchioles or nasal passages. Specifically, aerosol includes a gas-borne suspension of droplets, as can be produced in a metered dose inhaler or nebulizer, or in a mist sprayer. Aerosol also includes a dry powder composition suspended in air or other carrier gas, which can be delivered by insufflation from an inhaler device, for example. See Ganderton & Jones, *Drug Delivery to the Respiratory Tract*, Ellis Horwood (1987); Gonda (1990) *Critical Reviews in Therapeutic Drug Carrier Systems* 6:273-313; and Raeburn, et al. (1992) *J. Pharmacol. Toxicol. Methods* 27:143-159. Aerosols of liquid particles containing the compound can be produced by any suitable means, such as with a pressure-driven aerosol nebulizer or an ultrasonic nebulizer, as is known to those of skill in the art. See, e.g., U.S. Pat. No. 4,501,729. Aerosols of solid particles containing the compound can likewise be produced with any solid particulate medicament aerosol generator, by techniques known in the pharmaceutical art.

Alternatively, one can administer the compound in a local rather than systemic manner, for example, in a depot or sustained-release formulation.

Further, the present invention provides liposomal formulations of the compounds disclosed herein and salts thereof. The technology for forming liposomal suspensions is well-known in the art. When the compound or salt thereof is an aqueous-soluble salt, using conventional liposome technology, the same can be incorporated into lipid vesicles. In such an instance, due to the water solubility of the compound or salt, the compound or salt will be substantially entrained within the hydrophilic center or core of the liposomes. The lipid layer employed can be of any conventional composition and can either contain cholesterol or can be cholesterol-free. When the compound or salt of interest is water-insoluble, again employing conventional liposome formation technology, the salt can be substantially entrained within the hydrophobic lipid bilayer which forms the structure of the liposome. In either instance, the liposomes which are produced can be reduced in size, as through the use of standard sonication and homogenization techniques.

A liposomal formulation containing a compound disclosed herein or salt thereof, can be lyophilized to produce a lyophilizate which can be reconstituted with a carrier, such as water, to regenerate a liposomal suspension.

In particular embodiments, the compound is administered to the subject in an effective amount, as that term is defined herein. Dosages of active compounds can be determined by methods known in the art, see, e.g., Remington: The Science and Practice of Pharmacy, Alfonso R. Gennaro, editor, 20th ed. Lippincott Williams & Wilkins: Philadelphia, Pa., 2000. The selected effective dosage level will depend upon a variety of factors including the activity of the particular compound of the present invention employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well-known in the medical arts.

A physician or veterinarian having ordinary skill in the art can readily determine and prescribe the effective amount of the pharmaceutical composition required for prevention or treatment in an animal subject such as a human, agriculturally-important animal, pet or zoological animal.

The invention is described in greater detail by the following non-limiting examples.

EXAMPLE 1

S. cerevisiae Strains

Yeast diploid strain BY165, heterozygous for qns1 deletion and haploid BY165-1d carrying a chromosomal deletion of qns1 gene, transformed with plasmid pB175 containing QNS1 and URA3 is known in the art (Bieganowski, et al. (2003) supra). Genetic deletions were introduced by direct transformation with PCR products (Brachmann, et al. (1998) *Yeast* 14:115-132) generated from primers. After 24 hours of growth on complete media, cells were plated on media containing 5-fluoroorotic acid (Boeke, et al. (1987) *Methods Enzymol.* 154:164-175). The ado1 disruption cassette was constructed by PCR with primers 7041 (5'-CTA TTT AGA GTA AGG ATA TTT TTT CGG AAG GGT AAG AGG GAC CAA CTT CTT CTG TGC GGT ATT TCA CAC CG-3'; SEQ ID NO:10) and 7044 (5'-ATG ACC GCA CCA TTG GTA GTA TTG GGT AAC CCA CTT TTA GAT TTC CAA GCA GAT TGT ACT GAG AGT GCA C-3'; SEQ ID NO:11) and plasmid pRS413 as a template. Yeast strain BY165 was transformed with this PCR product, and homologous recombination in histidine prototrophic transformants was confirmed by PCR with primers 7042 (5'-AAG CTA GAG GGA ACA CGT AGA G-3'; SEQ ID NO:12) and 7043 (5'-TTA TCT TGT GCA GGG TAG AAC C-3'; SEQ ID NO:13). This strain was transformed with plasmid pB175 and subjected to sporulation and tetrad dissection. Haploid strain BY237, carrying qns1 and ado1 deletions and plasmid, was selected for further experiments. The urk1 deletion was introduced into strain BY237 by transformation with the product of the PCR amplification that used pRS415 as a template and PCR primers 7051 (5'-CGA TCT TCA TCA TTT ATT TCA ATT TTA GAC GAT GAA ACA AGA GAC ACA TTA GAT TGT ACT GAG AGT GCA C-3'; SEQ ID NO:14) and 7052 (5'-AAA ATA CTT TGA ATC AAA AAA TCT GGT CAA TGC CCA TTT GTA TTG ATG ATC TGT GCG GTA TTT CAC ACC G-3'; SEQ ID NO:15). Disruption was confirmed by PCR with primers 7053 (5'-ATG TCC CAT CGT ATA GCA CCT TCC-3'; SEQ ID NO:16) and 7054 (5'-GCC TCT AAT TAT TCT CAA TCA CAA CC-3'; SEQ ID NO:17), and the resulting strain was designated BY247. The rbk1 disruption cassette was constructed by PCR with primers 7063 (5'-AAA CTT TCA GGG CTA ACC ACT TCG AAA CAC ATG CTG GTG GTA AGG GAT TGA GAT TGT ACT GAG AGT GCA C-3'; SEQ ID NO:18) and 7065 (5'-GAA CAG AAA AGC ACC CCT CTC GAA CCC AAA GTC ATA ACC ACA ATT CCT CTC TGT GCG GTA TTT CAC ACC G-3'; SEQ ID NO:19) and plasmid pRS411 as a template. Disruption was introduced into strain BY242 by transformation with the product of this reaction and confirmed by PCR with primers 7062 (5'-GGA TAG ATT ACC TAA CGC TGG AG-3'; SEQ ID NO:20) and 7064 (5'-TTG TAC TTC AGG GCT TTC GTG C-3'; SEQ ID NO:21). The resulting strain, carrying deletions of qns1, ado1, urk1 and rbk1 genes was designated BY252. A yeast strain carrying disruption of the NRK1 locus was made by transformation of the strain BY165-1d with the HIS3 marker introduced into disruption cassette by PCR with primers 4750 (5'-AAT AGC GTG CAA AAG CTA TCG AAG TGT GAG CTA GAG TAG AAC CTC AAA ATA GAT TGT ACT GAG AGT GCA C-3'; SEQ ID NO:22) and 4751 (5'-CTA ATC CTT ACA AAG CTT TAG AAT CTC TTG GCA CAC CCA GCT TAA AGG TCT GTG CGG TAT TTC ACA CCG-3'; SEQ ID NO:23). Correct integration of the HIS3 marker into NRK1 locus was confirmed by PCR with primers 4752 (5'-ACC AAC TTG CAT TTT AGG CTG TTC-3'; SEQ ID NO:24) and 4753 (5'-TAA GTT ATC TAT CGA GGT ACA CAT TC-3'; SEQ ID NO:25).

EXAMPLE 2

Nicotinamide Riboside and Whey Preparations

NMN (39.9 mg; Sigma, St. Louis, Mo.) was treated with 1250 units of calf intestinal alkaline phosphatase (Sigma) for 1 hour at 37° C. in 1 mL 100 mM NaCl, 20 mM Tris pH 8.0, 5 mM $MgCl_2$. Hydrolysis of NMN to nicotinamide riboside was verified by HPLC and phosphatase was removed by centrifuging the reaction through a 5,000 Da filter (Millipore, Billerica, Mass.). A whey vitamin fraction of commercial nonfat cow's milk was prepared by adjusting the pH to 4 with HCl, stirring at 55° C. for 10 minutes, removal of denatured casein by centrifugation, and passage through a 5,000 Da filter. In yeast media, nicotinamide riboside was used at 10 μM and whey vitamin fraction at 50% by volume.

EXAMPLE 3

Yeast GST-ORF Library

Preparation of the fusion protein library was in accordance with well-established methods (Martzen, et al. (1999) supra; Phizicky, et al. (2002) *Methods Enzymol.* 350:546-559) at a 0.5 liter culture scale for each of the 64 pools of 90-96 protein constructs. Ten percent of each pool preparation was assayed for Nrk activity in overnight incubations.

EXAMPLE 4

Nicotinamide Riboside Phosphorylation Assays

Reactions (0.2 mL) containing 100 mM NaCl, 20 mM NaHEPES pH 7.2, 5 mM β-mercaptoethanol, 1 mM ATP, 5 mM $MgCl_2$, and 500 μM nicotinamide riboside or alternate nucleoside, were incubated at 30° C. and terminated by addition of EDTA to 20 mM and heating for 2 minutes at 100° C. Specific activity assays, containing 50 ng to 6 μg enzyme depending on the enzyme and substrate, were incubated for 30 minutes at 30° C. to maintain initial rate conditions. Reaction products were analyzed by HPLC on a strong anion exchange column with a 10 mM to 750 mM gradient of $KPO_4$ pH 2.6.

EXAMPLE 5

NRK Gene and cDNA Cloning and Enzyme Purification

The *S. cerevisiae* NRK1 gene was amplified from total yeast DNA with primers 7448 (5'-CGC TGC ACA TAT GAC TTC GAA AAA AGT GAT ATT AGT TGC-3'; SEQ ID NO:26) and 7449 (5'-CCG TCT CGA GCT AAT CCT TAC AAA GCT TTA GAA TCT CTT GG-3'; SEQ ID NO:27). The amplified DNA fragment was cloned in vector pSG04 (Ghosh and Lowenstein (1997) *Gene* 176:249-255) for *E. coli* expression using restriction sites for NdeI and XhoI included in primer sequences and the resulting plasmid was designated pB446. Samples of cDNA made from human lymphocytes and spleen were used as a template for amplification of human NRK1 using primers 4754 (5'-CCG GCC CAT GGC GCA CCA CCA TCA CCA CCA TCA TAT GAA AAC ATT TAT CAT TGG AAT CAG TGG-3'; SEQ ID NO:28) and 4755 (5'-GCG GGG ATC CTT ATG CTG TCA CTT GCA AAC ACT TTT GC-3'; SEQ ID NO:29). For *E. coli* expression, PCR amplicons from this reaction were cloned into restriction sites NcoI and BamHI of vector pMR103 (Munson, et al. (1994) *Gene* 144:59-62) resulting in plasmid pB449. Subsequently, plasmid pB449 was used as a template for PCR with primers 7769 (5'-CCG CGG ATC CAT GAA AAC ATT TAT CAT TGG AAT CAG TGG-3'; SEQ ID NO:30) and 7770 (5'-GCC GCT CGA GTT ATG CTG TCA CTT GCA AAC ACT T-3'; SEQ ID NO:31). The product of this amplification was cloned between BamHI and XhoI sites of vector p425GAL1 (Mumberg, et al. (1994) *Nucleic Acids Res.* 22:5767-5768) and the resulting plasmid carrying human NRK1 gene under GAL1 promoter control was designated pB450. Human NRK2 cDNA was amplified with primers 7777 (5'-GGC AGG CAT ATG AAG CTC ATC GTG GGC ATC G-3'; SEQ ID NO:32) and 7776 (5'-GCT CGC TCG AGT CAC ATG CTG TCC TGC TGG GAC-3'; SEQ ID NO:33). The amplified fragment was digested with NdeI and XhoI enzymes and cloned in plasmid pSGA04 for *E. coli* expression. His-tagged enzymes were purified with Ni-NTA agarose.

What is claimed is:

1. A composition comprising isolated nicotinamide riboside in combination with one or more of tryptophan, nicotinic acid, or nicotinamide, wherein said combination is in admixture with a carrier comprising a sugar, starch, cellulose, powdered tragacanth, malt, gelatin, talc, cocoa butter, suppository wax, oil, glycol, polyol, ester, agar, buffering agent, alginic acid, isotonic saline, Ringer's solution, ethyl alcohol, polyester, polycarbonate, or polyanhydride, wherein said composition is formulated for oral administration and increases NAD+ biosynthesis upon oral administration.

2. The composition of claim 1, wherein the nicotinamide riboside is isolated from a natural or synthetic source.

3. The composition of claim 1, wherein the formulation comprises a tablet, troche, capsule, elixir, suspension, syrup, wafer, chewing gum, or food.

* * * * *

SEQUENCE LISTING

<160> NUMBER OF SEQ ID NOS: 34

<210> SEQ ID NO 1
<211> LENGTH: 1199
<212> TYPE: DNA
<213> ORGANISM: Saccharomyces cerevisiae

<400> SEQUENCE: 1

| | | | | | |
|---|---|---|---|---|---|
| tagcacctga | gtatatatct | gacataaaaa | gatttctgaa | gttatcgtca | gataagaaga | 60 |
| tggagtcaaa | atgtaaacaa | taactttaac | ctatataaat | tttcttacat | ttgcttttaa | 120 |
| atactcgaag | atttgcattg | aacgatcgtt | gccgttgact | catttgaaac | agaaaaacaa | 180 |
| tacacgcagg | aaaggaacgg | cagttggtct | gagaaacaaa | accaacttgc | attttaggct | 240 |
| gttccgatag | tttatcagag | taagggaaaa | aatagcgtgc | aaaagctatc | gaagtgtgag | 300 |
| ctagagtaga | acctcaaaat | atgacttcga | aaaagtgat | attagttgca | ttgagtggat | 360 |
| gctcctccag | tggtaagacg | acaattgcga | aacttacagc | aagtttattc | acgaaggcta | 420 |
| cattaattca | tgaagatgac | ttttacaaac | atgataatga | agtgccagta | gatgctaaat | 480 |
| ataacattca | aaattgggat | cgccagaag | ctcttgattt | taaacttttc | ggtaaagaat | 540 |
| tagatgtgat | caaacaaact | ggtaaaatag | ccaccaaact | tatacacaat | aacaacgtag | 600 |
| atgatccctt | tacaaagttc | acattgata | gacaagtttg | ggacgagtta | aaggctaagt | 660 |
| atgactctat | taatgacgac | aaatatgaag | ttgtaattgt | agatgggttt | atgattttca | 720 |
| ataatactgg | aatatcaaaa | aaatttgatt | tgaagatatt | agtgcgtgct | ccctatgaag | 780 |
| tactaaaaaa | aaggagggct | tccagaaaag | gataccagac | tttggattct | ttctgggtgg | 840 |
| atccgccgta | ttatttcgac | gaatttgtgt | atgaatctta | tcgtgcaaat | catgcgcagt | 900 |
| tatttgttaa | tggagacgta | gaaggtttac | tagacccaag | gaagtcaaag | aatataaaag | 960 |
| agttcataaa | tgatgatgac | actccaattg | cgaaaccttt | aagctgggtg | tgccaagaga | 1020 |
| ttctaaagct | ttgtaaggat | taggaaagcg | ccacaaaatc | gatgagaagt | ataaaaaaaa | 1080 |
| aaaagtaaaa | acaataaaaa | taagaatgtg | tacctcgata | gataacttaa | ataagacaat | 1140 |
| ttcagaacca | caatattgat | aacaccatcc | cgattttga | aattattttt | ttggtgtaa | 1199 |

<210> SEQ ID NO 2
<211> LENGTH: 1172
<212> TYPE: DNA
<213> ORGANISM: Homo sapiens

<400> SEQUENCE: 2

| | | | | | |
|---|---|---|---|---|---|
| aaaggggcct | ctggtgaccg | cccctacctg | gcatccctct | aacccaggag | gagcgtgggg | 60 |
| aaaggggctg | tgggcctctc | ggggagcgag | ctgcgggtag | cggcgcactg | ggtacaggcg | 120 |
| cgcgcttggc | tgtcgcctct | tccgctgtgt | ttgggaggac | tcgaactggc | gccaggaaat | 180 |
| attaggaagc | tgtgattttc | aaagctaatt | atgaaaacat | ttatcattgg | aatcagtggt | 240 |
| gtgacaaaca | gtggcaaaac | aacactggct | aagaatttgc | agaaacacct | cccaaattgc | 300 |
| agtgtcatat | ctcaggatga | tttcttcaag | ccagagtctg | agatagagac | agataaaaat | 360 |
| ggattttttgc | agtacgatgt | gcttgaagca | cttaacatgg | aaaaaatgat | gtcagccatt | 420 |
| tcctgctgga | tggaaagcgc | aagacactct | gtggtatcaa | cagaccagga | aagtgctgag | 480 |
| gaaattccca | ttttaatcat | cgaaggtttt | cttctttta | attataagcc | ccttgacact | 540 |
| atatggaata | gaagctattt | cctgactatt | ccatatgaag | aatgtaaaag | gaggaggagt | 600 |
| acaagggtct | atcagcctcc | agactctccg | ggatactttg | atggccatgt | gtggcccatg | 660 |
| tatctaaagt | acagacaaga | aatgcaggac | atcacatggg | aagttgtgta | cctggatgga | 720 |
| acaaaatctg | aagaggacct | cttttttgcaa | gtatatgaag | atctaataca | agaactagca | 780 |
| aagcaaaagt | gtttgcaagt | gacagcataa | agacggaaca | caacaaatcc | ttcctgaagt | 840 |
| gaattaggaa | actccaagga | gtaatttaag | aaccttcacc | aagatacaat | gtatactgtg | 900 |

```
gtacaatgac agccattgtt tcatatgttt gattttatt gcacatggtt ttcccaacat    960
gtggaacaat aaatatccat gccaatggac aggactgtac cttagcaagt tgctccctct   1020
ccagggagcg catagataca gcagagctca cagtgagtca gaaagtctcc actttctgaa   1080
catagctcta taacaatgat tgtcaaactt ttctaactgg agctcagagt aagaaataaa   1140
gattacatca aatccaaaa aaaaaaaaaa aa                                  1172
```

<210> SEQ ID NO 3
<211> LENGTH: 1134
<212> TYPE: DNA
<213> ORGANISM: Homo sapiens

<400> SEQUENCE: 3

```
aatcatcttg ttggccctga cctcgttgga aaacgaagct ccccgcaggg tcccggcctc     60
tagggctgct gtgcgggcgg gggtggcctg gagctatttc cattcggcgg cgggaacagg    120
tgccggcgcc tccgccccat ccccaggggc cgcctccccc ggggcggcct ccaggctgcc    180
gagacctata aaggcgccag gttttctcaa tgaagccggg acgcactccg gagcgcactg    240
cgtggtcgca ccctacccgg gctgccttgg aagtcgtccc cgccgcccct ccgcaccggc    300
atgaagctca tcgtgggcat cggaggcatg accaacggcg gcaagaccac gctgaccaac    360
agcctgctca gagccctgcc caactgctgc gtgatccatc aggatgactt cttcaagccc    420
caagaccaaa tagcagttgg ggaagacggc ttcaaacagt gggacgtgct ggagtctctg    480
gacatggagg ccatgctgga caccgtgcag gcctggctga gcagcccgca gaagtttgcc    540
cgtgcccacg gggtcagcgt ccagccagag gcctcggaca cccacatcct cctcctggaa    600
ggcttcctgc tctacagcta caagcccctg gtggacttgt acagccgccg gtacttcctg    660
accgtcccgt atgaagagtg caagtggagg agaagtaccc gcaactacac agtccctgat    720 cccccggcc tcttcgatgg ccacgtgtgg cccatgtacc agaagtatag caggagatg    780 gaggccaacg gtgtggaagt ggtctacctg gacggcatga agtcccgaga ggagctcttc    840
cgtgaagtcc tggaagacat tcagaactcg ctgctgaacc gctcccagga atcagccccc    900
tccccggctc gcccagccag gacacaggga cccggacgcg gatgcggcca cagaacggcc    960
aggcctgcag cgtcccagca ggacagcatg tgagcgtttc cctatggggg tgtctgtacg   1020
taggagagtg gaggccccac tcccagttgg gcgtcccgga gctcagggac tgagcccaa    1080 gacgcctctg taacctcgct gcagcttcag tagtaaactg ggtcctgttt tttt          1134
```

<210> SEQ ID NO 4
<211> LENGTH: 240
<212> TYPE: PRT
<213> ORGANISM: Saccharomyces cerevisiae

<400> SEQUENCE: 4

```
Met Thr Ser Lys Lys Val Ile Leu Val Ala Leu Ser Gly Cys Ser Ser
  1               5                  10                  15

Ser Gly Lys Thr Thr Ile Ala Lys Leu Thr Ala Ser Leu Phe Thr Lys
                 20                  25                  30

Ala Thr Leu Ile His Glu Asp Asp Phe Tyr Lys His Asp Asn Glu Val
             35                  40                  45

Pro Val Asp Ala Lys Tyr Asn Ile Gln Asn Trp Asp Ser Pro Glu Ala
         50                  55                  60

Leu Asp Phe Lys Leu Phe Gly Lys Glu Leu Asp Val Ile Lys Gln Thr
 65                  70                  75                  80
```

```
Gly Lys Ile Ala Thr Lys Leu Ile His Asn Asn Val Asp Asp Pro
                85                  90                  95

Phe Thr Lys Phe His Ile Asp Arg Gln Val Trp Asp Glu Leu Lys Ala
            100                 105                 110

Lys Tyr Asp Ser Ile Asn Asp Asp Lys Tyr Glu Val Ile Val Asp
            115                 120                 125

Gly Phe Met Ile Phe Asn Asn Thr Gly Ile Ser Lys Lys Phe Asp Leu
            130                 135                 140

Lys Ile Leu Val Arg Ala Pro Tyr Glu Val Leu Lys Lys Arg Arg Ala
145                 150                 155                 160

Ser Arg Lys Gly Tyr Gln Thr Leu Asp Ser Phe Trp Val Asp Pro Pro
            165                 170                 175

Tyr Tyr Phe Asp Glu Phe Val Tyr Glu Ser Tyr Arg Ala Asn His Ala
            180                 185                 190

Gln Leu Phe Val Asn Gly Asp Val Glu Gly Leu Leu Asp Pro Arg Lys
            195                 200                 205

Ser Lys Asn Ile Lys Glu Phe Ile Asn Asp Asp Thr Pro Ile Ala
            210                 215                 220

Lys Pro Leu Ser Trp Val Cys Gln Glu Ile Leu Lys Leu Cys Lys Asp
225                 230                 235                 240

<210> SEQ ID NO 5
<211> LENGTH: 199
<212> TYPE: PRT
<213> ORGANISM: Homo sapiens

<400> SEQUENCE: 5

Met Lys Thr Phe Ile Ile Gly Ile Ser Gly Val Thr Asn Ser Gly Lys
1               5                   10                  15

Thr Thr Leu Ala Lys Asn Leu Gln Lys His Leu Pro Asn Cys Ser Val
            20                  25                  30

Ile Ser Gln Asp Asp Phe Phe Lys Pro Glu Ser Glu Ile Glu Thr Asp
            35                  40                  45

Lys Asn Gly Phe Leu Gln Tyr Asp Val Leu Glu Ala Leu Asn Met Glu
        50                  55                  60

Lys Met Met Ser Ala Ile Ser Cys Trp Met Glu Ser Ala Arg His Ser
65              70                  75                  80

Val Val Ser Thr Asp Gln Glu Ser Ala Glu Ile Pro Ile Leu Ile
            85                  90                  95

Ile Glu Gly Phe Leu Leu Phe Asn Tyr Lys Pro Leu Asp Thr Ile Trp
            100                 105                 110

Asn Arg Ser Tyr Phe Leu Thr Ile Pro Tyr Glu Glu Cys Lys Arg Arg
            115                 120                 125

Arg Ser Thr Arg Val Tyr Gln Pro Pro Asp Ser Pro Gly Tyr Phe Asp
            130                 135                 140

Gly His Val Trp Pro Met Tyr Leu Lys Tyr Arg Gln Glu Met Gln Asp
145                 150                 155                 160

Ile Thr Trp Glu Val Val Tyr Leu Asp Gly Thr Lys Ser Glu Glu Asp
            165                 170                 175

Leu Phe Leu Gln Val Tyr Glu Asp Leu Ile Gln Glu Leu Ala Lys Gln
            180                 185                 190

Lys Cys Leu Gln Val Thr Ala
            195

<210> SEQ ID NO 6
<211> LENGTH: 230
```

```
<212> TYPE: PRT
<213> ORGANISM: Homo sapiens

<400> SEQUENCE: 6

Met Lys Leu Ile Val Gly Ile Gly Gly Met Thr Asn Gly Gly Lys Thr
1               5                   10                  15

Thr Leu Thr Asn Ser Leu Leu Arg Ala Leu Pro Asn Cys Cys Val Ile
            20                  25                  30

His Gln Asp Asp Phe Phe Lys Pro Gln Asp Gln Ile Ala Val Gly Glu
        35                  40                  45

Asp Gly Phe Lys Gln Trp Asp Val Leu Glu Ser Leu Asp Met Glu Ala
    50                  55                  60

Met Leu Asp Thr Val Gln Ala Trp Leu Ser Ser Pro Gln Lys Phe Ala
65                  70                  75                  80

Arg Ala His Gly Val Ser Val Gln Pro Glu Ala Ser Asp Thr His Ile
                85                  90                  95

Leu Leu Leu Glu Gly Phe Leu Leu Tyr Ser Tyr Lys Pro Leu Val Asp
            100                 105                 110

Leu Tyr Ser Arg Arg Tyr Phe Leu Thr Val Pro Tyr Glu Glu Cys Lys
        115                 120                 125

Trp Arg Arg Ser Thr Arg Asn Tyr Thr Val Asp Pro Pro Gly Leu
    130                 135                 140

Phe Asp Gly His Val Trp Pro Met Tyr Gln Lys Tyr Arg Gln Glu Met
145                 150                 155                 160

Glu Ala Asn Gly Val Glu Val Val Tyr Leu Asp Gly Met Lys Ser Arg
                165                 170                 175

Glu Glu Leu Phe Arg Glu Val Leu Glu Asp Ile Gln Asn Ser Leu Leu
            180                 185                 190

Asn Arg Ser Gln Glu Ser Ala Pro Ser Pro Ala Arg Pro Ala Arg Thr
        195                 200                 205

Gln Gly Pro Gly Arg Gly Cys Gly His Arg Thr Ala Arg Pro Ala Ala
    210                 215                 220

Ser Gln Gln Asp Ser Met
225                 230

<210> SEQ ID NO 7
<211> LENGTH: 229
<212> TYPE: PRT
<213> ORGANISM: Schizosaccharomyces pombe

<400> SEQUENCE: 7

Met Thr Arg Lys Thr Ile Ile Val Gly Val Ser Gly Ala Ser Cys Ser
1               5                   10                  15

Gly Lys Ser Thr Leu Cys Gln Leu Leu His Ala Ile Phe Glu Gly Ser
            20                  25                  30

Ser Leu Val His Glu Asp Asp Phe Tyr Lys Thr Asp Ala Glu Ile Pro
        35                  40                  45

Val Lys Asn Gly Ile Ala Asp Trp Asp Cys Gln Glu Ser Leu Asn Leu
    50                  55                  60

Asp Ala Phe Leu Glu Asn Leu His Tyr Ile Arg Asp His Gly Val Leu
65                  70                  75                  80

Pro Thr His Leu Arg Asn Arg Glu Asn Lys Asn Val Ala Pro Glu Ala
                85                  90                  95

Leu Ile Glu Tyr Ala Asp Ile Ile Lys Glu Phe Lys Ala Pro Ala Ile
            100                 105                 110

Pro Thr Leu Glu Gln His Leu Val Phe Val Asp Gly Phe Met Met Tyr
```

-continued

```
                115                 120                 125
Val Asn Glu Asp Leu Ile Asn Ala Phe Asp Ile Arg Leu Met Leu Val
    130                 135                 140

Thr Asp Phe Asp Thr Leu Lys Arg Arg Glu Ala Arg Thr Gly Tyr
145                 150                 155                 160

Ile Thr Leu Glu Gly Phe Trp Gln Asp Pro His Tyr Phe Glu Asn
                165                 170                 175

Tyr Val Trp Pro Gly Tyr Val His Gly His Ser His Leu Phe Val Asn
                180                 185                 190

Gly Asp Val Thr Gly Lys Leu Leu Asp Lys Arg Ile Gln Leu Ser Pro
                195                 200                 205

Ser Ser Lys Met Ser Val Arg Asp Asn Val Gln Trp Ala Ile Asn Ser
    210                 215                 220

Ile Leu Asn Ala Leu
225

<210> SEQ ID NO 8
<211> LENGTH: 243
<212> TYPE: PRT
<213> ORGANISM: Saccharomyces cerevisiae

<400> SEQUENCE: 8

Thr Pro Tyr Ile Ile Gly Ile Gly Gly Ala Ser Gly Ser Gly Lys Thr
1               5                   10                  15

Ser Val Ala Ala Lys Ile Val Ser Ser Ile Asn Val Pro Trp Thr Val
                20                  25                  30

Leu Ile Ser Leu Asp Asn Phe Tyr Asn Pro Leu Gly Pro Glu Asp Arg
            35                  40                  45

Ala Arg Ala Phe Lys Asn Glu Tyr Asp Phe Asp Glu Pro Asn Ala Ile
        50                  55                  60

Asn Leu Asp Leu Ala Tyr Lys Cys Ile Leu Asn Leu Lys Glu Gly Lys
65                  70                  75                  80

Arg Thr Asn Ile Pro Val Tyr Ser Phe Val His His Asn Arg Val Pro
                85                  90                  95

Asp Lys Asn Ile Val Ile Tyr Gly Ala Ser Val Val Ile Glu Gly
            100                 105                 110

Ile Tyr Ala Leu Tyr Asp Arg Arg Leu Leu Asp Leu Met Asp Leu Lys
            115                 120                 125

Ile Tyr Val Asp Ala Asp Leu Asp Val Cys Leu Ala Arg Arg Leu Ser
        130                 135                 140

Arg Asp Ile Val Ser Arg Gly Arg Asp Leu Asp Gly Cys Ile Gln Gln
145                 150                 155                 160

Trp Glu Lys Phe Val Lys Pro Asn Ala Val Lys Phe Val Lys Pro Thr
                165                 170                 175

Met Lys Asn Ala Asp Ala Ile Ile Pro Ser Met Ser Asp Asn Ala Thr
            180                 185                 190

Ala Val Asn Leu Ile Ile Asn His Ile Lys Ser Lys Leu Glu Leu Lys
            195                 200                 205

Ser Asn Glu His Leu Arg Glu Leu Ile Lys Leu Gly Ser Ser Pro Ser
    210                 215                 220

Gln Asp Val Leu Asn Arg Asn Ile Ile His Glu Leu Pro Pro Thr Asn
225                 230                 235                 240

Gln Val Leu

<210> SEQ ID NO 9
```

<211> LENGTH: 232
<212> TYPE: PRT
<213> ORGANISM: Escherichia coli

<400> SEQUENCE: 9

```
Gln Thr Leu Met Thr Pro Tyr Leu Gln Phe Asp Arg Asn Gln Trp Ala
1               5                   10                  15

Ala Leu Arg Asp Ser Val Pro Met Thr Leu Ser Glu Asp Glu Ile Ala
            20                  25                  30

Arg Leu Lys Gly Ile Asn Glu Asp Leu Ser Leu Glu Glu Val Ala Glu
        35                  40                  45

Ile Tyr Leu Pro Leu Ser Arg Leu Leu Asn Phe Tyr Ile Ser Ser Asn
    50                  55                  60

Leu Arg Arg Gln Ala Val Leu Glu Gln Phe Leu Gly Thr Asn Gly Gln
65                  70                  75                  80

Arg Ile Pro Tyr Ile Ile Ser Ile Ala Gly Ser Val Ala Val Gly Lys
                85                  90                  95

Ser Thr Thr Ala Arg Val Leu Gln Ala Leu Leu Ser Arg Trp Pro Glu
            100                 105                 110

His Arg Arg Val Glu Leu Ile Thr Thr Asp Gly Phe Leu His Pro Asn
        115                 120                 125

Gln Val Leu Lys Glu Arg Gly Leu Met Lys Lys Gly Phe Pro Glu
    130                 135                 140

Ser Tyr Asp Met His Arg Leu Val Lys Phe Val Ser Asp Leu Lys Ser
145                 150                 155                 160

Gly Val Pro Asn Val Thr Ala Pro Val Tyr Ser His Leu Ile Tyr Asp
                165                 170                 175

Val Ile Pro Asp Gly Asp Lys Thr Val Val Gln Pro Asp Ile Leu Ile
            180                 185                 190

Leu Glu Gly Leu Asn Val Leu Gln Ser Gly Met Asp Tyr Pro His Asp
        195                 200                 205

Pro His His Val Phe Val Ser Asp Phe Val Asp Phe Ser Ile Tyr Val
    210                 215                 220

Asp Ala Pro Glu Asp Leu Leu Gln
225                 230
```

<210> SEQ ID NO 10
<211> LENGTH: 71
<212> TYPE: DNA
<213> ORGANISM: Artificial Sequence
<220> FEATURE:
<223> OTHER INFORMATION: Synthetic primer

<400> SEQUENCE: 10
ctatttagag taaggatatt ttttcggaag ggtaagaggg accaacttct tctgtgcggt    60
atttcacacc g                                                        71

<210> SEQ ID NO 11
<211> LENGTH: 70
<212> TYPE: DNA
<213> ORGANISM: Artificial Sequence
<220> FEATURE:
<223> OTHER INFORMATION: Synthetic primer

<400> SEQUENCE: 11
atgaccgcac cattggtagt attgggtaac ccacttttag atttccaagc agattgtact    60
gagagtgcac                                                          70

```
<210> SEQ ID NO 12
<211> LENGTH: 22
<212> TYPE: DNA
<213> ORGANISM: Artificial Sequence
<220> FEATURE:
<223> OTHER INFORMATION: Synthetic primer

<400> SEQUENCE: 12
aagctagagg gaacacgtag ag                                              22

<210> SEQ ID NO 13
<211> LENGTH: 22
<212> TYPE: DNA
<213> ORGANISM: Artificial Sequence
<220> FEATURE:
<223> OTHER INFORMATION: Synthetic primer

<400> SEQUENCE: 13
ttatcttgtg cagggtagaa cc                                              22

<210> SEQ ID NO 14
<211> LENGTH: 70
<212> TYPE: DNA
<213> ORGANISM: Artificial Sequence
<220> FEATURE:
<223> OTHER INFORMATION: Synthetic primer

<400> SEQUENCE: 14
cgatcttcat catttatttc aattttagac gatgaaacaa gagacacatt agattgtact     60
gagagtgcac                                                            70

<210> SEQ ID NO 15
<211> LENGTH: 70
<212> TYPE: DNA
<213> ORGANISM: Artificial Sequence
<220> FEATURE:
<223> OTHER INFORMATION: Synthetic primer

<400> SEQUENCE: 15
aaaatacttt gaatcaaaaa atctggtcaa tgcccatttg tattgatgat ctgtgcggta     60
tttcacaccg                                                            70

<210> SEQ ID NO 16
<211> LENGTH: 24
<212> TYPE: DNA
<213> ORGANISM: Artificial Sequence
<220> FEATURE:
<223> OTHER INFORMATION: Synthetic primer

<400> SEQUENCE: 16
atgtcccatc gtatagcacc ttcc                                            24

<210> SEQ ID NO 17
<211> LENGTH: 26
<212> TYPE: DNA
<213> ORGANISM: Artificial Sequence
<220> FEATURE:
<223> OTHER INFORMATION: Synthetic primer

<400> SEQUENCE: 17
gcctctaatt attctcaatc acaacc                                          26

<210> SEQ ID NO 18
<211> LENGTH: 70
<212> TYPE: DNA
<213> ORGANISM: Artificial Sequence
```

```
<220> FEATURE:
<223> OTHER INFORMATION: Synthetic primer

<400> SEQUENCE: 18
aaactttcag ggctaaccac ttcgaaacac atgctggtgg taagggattg agattgtact    60
gagagtgcac                                                           70

<210> SEQ ID NO 19
<211> LENGTH: 70
<212> TYPE: DNA
<213> ORGANISM: Artificial Sequence
<220> FEATURE:
<223> OTHER INFORMATION: Synthetic primer

<400> SEQUENCE: 19
gaacagaaaa gcacccctct cgaacccaaa gtcataacca caattcctct ctgtgcggta    60
tttcacaccg                                                           70

<210> SEQ ID NO 20
<211> LENGTH: 23
<212> TYPE: DNA
<213> ORGANISM: Artificial Sequence
<220> FEATURE:
<223> OTHER INFORMATION: Synthetic primer

<400> SEQUENCE: 20
ggatagatta cctaacgctg gag                                            23

<210> SEQ ID NO 21
<211> LENGTH: 22
<212> TYPE: DNA
<213> ORGANISM: Artificial Sequence
<220> FEATURE:
<223> OTHER INFORMATION: Synthetic primer

<400> SEQUENCE: 21
ttgtacttca gggctttcgt gc                                             22

<210> SEQ ID NO 22
<211> LENGTH: 70
<212> TYPE: DNA
<213> ORGANISM: Artificial Sequence
<220> FEATURE:
<223> OTHER INFORMATION: Synthetic primer

<400> SEQUENCE: 22
aatagcgtgc aaaagctatc gaagtgtgag ctagagtaga acctcaaaat agattgtact    60
gagagtgcac                                                           70

<210> SEQ ID NO 23
<211> LENGTH: 69
<212> TYPE: DNA
<213> ORGANISM: Artificial Sequence
<220> FEATURE:
<223> OTHER INFORMATION: Synthetic primer

<400> SEQUENCE: 23
ctaatcctta caaagcttta gaatctcttg gcacacccag cttaaaggtc tgtgcggtat    60
ttcacaccg                                                            69

<210> SEQ ID NO 24
<211> LENGTH: 24
<212> TYPE: DNA
<213> ORGANISM: Artificial Sequence
```

```
<220> FEATURE:
<223> OTHER INFORMATION: Synthetic primer

<400> SEQUENCE: 24
accaacttgc attttaggct gttc                                            24

<210> SEQ ID NO 25
<211> LENGTH: 26
<212> TYPE: DNA
<213> ORGANISM: Artificial Sequence
<220> FEATURE:
<223> OTHER INFORMATION: Synthetic primer

<400> SEQUENCE: 25
taagttatct atcgaggtac acattc                                          26

<210> SEQ ID NO 26
<211> LENGTH: 39
<212> TYPE: DNA
<213> ORGANISM: Artificial Sequence
<220> FEATURE:
<223> OTHER INFORMATION: Synthetic primer

<400> SEQUENCE: 26
cgctgcacat atgacttcga aaaaagtgat attagttgc                            39

<210> SEQ ID NO 27
<211> LENGTH: 41
<212> TYPE: DNA
<213> ORGANISM: Artificial Sequence
<220> FEATURE:
<223> OTHER INFORMATION: Synthetic primer

<400> SEQUENCE: 27
ccgtctcgag ctaatcctta caaagcttta gaatctcttg g                         41

<210> SEQ ID NO 28
<211> LENGTH: 63
<212> TYPE: DNA
<213> ORGANISM: Artificial Sequence
<220> FEATURE:
<223> OTHER INFORMATION: Synthetic primer

<400> SEQUENCE: 28
ccggcccatg gcgcaccacc atcaccacca tcatatgaaa acatttatca ttggaatcag     60
tgg                                                                   63

<210> SEQ ID NO 29
<211> LENGTH: 38
<212> TYPE: DNA
<213> ORGANISM: Artificial Sequence
<220> FEATURE:
<223> OTHER INFORMATION: Synthetic primer

<400> SEQUENCE: 29
gcggggatcc ttatgctgtc acttgcaaac acttttgc                             38

<210> SEQ ID NO 30
<211> LENGTH: 39
<212> TYPE: DNA
<213> ORGANISM: Artificial Sequence
<220> FEATURE:
<223> OTHER INFORMATION: Synthetic primer

<400> SEQUENCE: 30
ccgcggatcc atgaaaacat ttatcattgg aatcagtgg                            39
```

```
<210> SEQ ID NO 31
<211> LENGTH: 34
<212> TYPE: DNA
<213> ORGANISM: Artificial Sequence
<220> FEATURE:
<223> OTHER INFORMATION: Synthetic primer

<400> SEQUENCE: 31
gccgctcgag ttatgctgtc acttgcaaac actt                                  34

<210> SEQ ID NO 32
<211> LENGTH: 31
<212> TYPE: DNA
<213> ORGANISM: Artificial Sequence
<220> FEATURE:
<223> OTHER INFORMATION: Synthetic primer

<400> SEQUENCE: 32
ggcaggcata tgaagctcat cgtgggcatc g                                     31

<210> SEQ ID NO 33
<211> LENGTH: 33
<212> TYPE: DNA
<213> ORGANISM: Artificial Sequence
<220> FEATURE:
<223> OTHER INFORMATION: Synthetic primer

<400> SEQUENCE: 33
gctcgctcga gtcacatgct gtcctgctgg gac                                   33

<210> SEQ ID NO 34
<211> LENGTH: 9
<212> TYPE: PRT
<213> ORGANISM: Artificial Sequence
<220> FEATURE:
<223> OTHER INFORMATION: Eukaryotic nicotinamide riboside kinase
      consensus sequence
<220> FEATURE:
<221> NAME/KEY: MISC_FEATURE
<222> LOCATION: (1)..(2)
<223> OTHER INFORMATION: "Xaa" denotes an aliphatic amino acid residue
<220> FEATURE:
<221> NAME/KEY: MISC_FEATURE
<222> LOCATION: (3)..(3)
<223> OTHER INFORMATION: "Xaa" denotes His or Ser
<220> FEATURE:
<221> NAME/KEY: MISC_FEATURE
<222> LOCATION: (4)..(4)
<223> OTHER INFORMATION: "Xaa" denotes a hydrophilic amino acid residue
<220> FEATURE:
<221> NAME/KEY: MISC_FEATURE
<222> LOCATION: (8)..(8)
<223> OTHER INFORMATION: "Xaa" denotes an aromatic amino acid residue

<400> SEQUENCE: 34

Xaa Xaa Xaa Xaa Asp Asp Phe Xaa Lys
1               5
```